US006559122B1

(12) United States Patent
Oeswein et al.

(10) Patent No.: US 6,559,122 B1
(45) Date of Patent: May 6, 2003

(54) FORMULATED COMPOSITION

(75) Inventors: James Q. Oeswein, Moss Beach, CA (US); John R. Smikahl, Foster City, CA (US); Sharon X. Wang, San Mateo, CA (US); Douglas A. Yeung, Fremont, CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 09/539,310

(22) Filed: Mar. 30, 2000

Related U.S. Application Data
(60) Provisional application No. 60/128,392, filed on Apr. 8, 1999.

(51) Int. Cl.$^7$ .......................... A61K 38/28; C07K 17/00
(52) U.S. Cl. .............................. 514/3; 514/4; 514/866; 530/303; 530/399; 435/808
(58) Field of Search ................................ 514/3, 4, 866; 530/303, 399; 435/808

(56) References Cited

U.S. PATENT DOCUMENTS

| | | | |
|---|---|---|---|
| 4,608,364 A | 8/1986 | Grau ............................. | 514/4 |
| 4,876,242 A | 10/1989 | Applebaum et al. ........... | 514/3 |
| 4,988,675 A | 1/1991 | Froesch et al. ................ | 514/4 |
| 5,077,276 A | 12/1991 | Ballard et al. ................. | 514/12 |
| 5,091,173 A | 2/1992 | Buultjens et al. ............. | 424/70 |
| 5,164,370 A | 11/1992 | Ballard et al. ................. | 514/12 |
| 5,374,620 A | 12/1994 | Clark et al. .................... | 514/12 |
| 5,466,670 A | 11/1995 | Dunger et al. ................. | 514/12 |
| 5,470,828 A | 11/1995 | Ballard et al. ................. | 514/12 |
| 5,614,219 A | 3/1997 | Wunderlich et al. ........ | 424/472 |
| 5,681,814 A | 10/1997 | Clark et al. .................... | 514/12 |
| 5,756,463 A * | 5/1998 | Arhenius-Nyberg et al. .. | 514/12 |
| 5,783,556 A * | 7/1998 | Clark et al. .................... | 514/4 |
| 5,788,959 A | 8/1998 | Singh ........................ | 424/85.1 |

FOREIGN PATENT DOCUMENTS

| | | |
|---|---|---|
| EP | 123228 | 10/1984 |
| EP | 128733 | 12/1984 |
| EP | 288451 | 10/1988 |
| EP | 440989 A1 | 8/1991 |
| EP | 230869 B1 | 9/1992 |
| EP | 313343 B1 | 4/1995 |
| EP | 884053 | 12/1998 |
| WO | WO 87/01038 | 2/1987 |
| WO | WO 91/03253 | 3/1991 |
| WO | WO 91/18621 | 12/1991 |
| WO | WO 93/23071 | 11/1993 |
| WO | WO 94/15584 | 7/1994 |
| WO | WO 94/16722 | 8/1994 |
| WO | WO 95/34318 | 12/1995 |
| WO | WO 96/01124 | 1/1996 |
| WO | WO 96/01125 | 1/1996 |
| WO | WO 98/01161 | 1/1998 |
| WO | WO 98/06423 | 2/1998 |
| WO | WO 99/24063 | 5/1999 |

OTHER PUBLICATIONS

Tomas et al. Diabetes, vol. 45, pp. 170–177, Feb. 1996.*
Baxter, "The somatomedins: insulin–like growth factors" *Advances in Clinical Chemistry* 25:49–115 (1986).
Binoux, M., "Donnees recentes sur les somatomedines (Insulin–like growth factors)" *Annales d'Endocrinologie* 41:157–192 (1980).
Boulware et al., "Phosphate and Potassium Lowering Effects of Insulin–like Growth Factor–I in Humans: Comparison with Insulin" *The Endocrine Society, San Antonio*, (74th Annual Meeting) pp. 78:106 (abstract only) June. 1992).
Brange, J., "Insulin Preparations" *Galenics of Insulin, The Physico–chemical and Pharmaceutical Aspects of Insulin and Insulin Preparations*, New York: Springer–Verlag pp. 17–40 (1987).
Burgess et al., "Characterization of albumin–acacia complex coacervation" *Journal of Pharmacy & Pharmacology* 43(4):232–236 (Apr. 1991).
Campbell, "The Evolution of Insulin Therapy" *Pharmacy Times*, Romaine Pierson Vol. 59:40–44 (Oct. 1993).
Cheetham et al., "The Effects of Recombinant Human Insulin–like Growth Factor I on Growth Hormone Secretion in Adolescents With Insulin Dependent Diabetes Mellitus" *Clin. Endocrinol.* 40:515–522 (1994).
Cheetham et al., "The Effects of Recombinant Insulin–like Growth Factor I Adminstration on Growth Hormone Levels and Insulin Requirements in Adolescents With Type 1 (Insulin–dependent) Diabetes Mellitus" *Diabetologia* 36:678–681 (1993).
Clemmons and Van Wyk, "Somatomedin: physiological control and effects on cell proliferation" *Handbook Exp. Pharmacol.* 57:161–208 (1981).
Dodd et al., "Reversible adsorption of soluble hexameric insulin onto the surface of insulin crystals cocrystallized with protamine: an electrostatic interaction" *Pharmaceutical Research* 12(1):60–68 (Jan. 1995).
Dunger et al., "Insulin–like Growth Factors (IGFs) and IGF–I Treatment in the Adolescent With Insulin–dependent Diabetes Mellitus" *Metabolism* 44(10):119–123 (Supp. 4 1995).
Eizirik et al., "Insulin–Like Growth Factor I Does not Inhibit Insulin Secretion in Adult Human Pancreatic Islets in Tissue Culture" *European J. of Endocrinology* 133(2):248–250 (1995).
Elahi et al., "Hemodynamic and metabolic responses to human insulin–like growth factor I (IGF–I) in men" *Modern Concepts of Insulin–Like Growth Factors*, Spencer, EM, ed., New York: Elsevier Science Publ. Co. pp. 219–224 (1991).

(List continued on next page.)

Primary Examiner—Christopher S. F. Low
Assistant Examiner—Abdel A. Mohamed
(74) Attorney, Agent, or Firm—Janet E. Hasak

(57) ABSTRACT

A composition is disclosed that comprises a mixture of polypeptides of opposite charge and an excipient selected from the group consisting of arginine, lysine, glutamic acid, sodium dodecyl sulfate, beta-hydroxy cyclodextrin, and beta-cyclodextrin sulfobutyl ether.

32 Claims, 4 Drawing Sheets

OTHER PUBLICATIONS

Froesch et al., "Metabolic and Therapeutic Effects of Insulin–Like Growth Factor I" *Horm. Res.* 42:66–71 (1994).

Fuller et al., "Stimulation of Cardiac Protein Synthesis by Insulin–like Growth Factors" *Biochemical Society Transactions* 19:277S (1991).

Furnsinn et al., "Insulin–Like Growth Factor–I Inhibits Insulin and Amylin Secretion in Conscious Rats" *Endocrinology* 135(5):2144–2149 (1994).

Galloway and deShazo, "Insulin chemistry and pharmacology; insulin allergy, resistance, and lipodystrophy" *Diabetes Mellitus: Theory and Practice,* Rifkin and Porte, Jr. eds., Fourth edition, New York:Elsevier, Chapter 29, pp. 497–513 (1990).

Guler et al., "Effects of Insulin–like Growth Factor I in Man" *Acta Paediatr. Scand.* 367:52–54 (suppl. 1990).

Guler et al., "Short–term metabolic effects of recombinant human insulin–like growth factor I in healthy adults" *New England J. of Medicine* 317(3):137–140 (1987).

Gunn et al., "Anabolic steroids do not alter the effect of insulin and IGF–2 on protein breakdown in L6 muscle cells" *Biochemical Archives* 5:53–59 (1989).

Jabri et al., "Adverse effects of recombinant human insulin–like growth factor I in obese insulin–resistant type II diabetic patients" *Diabetes* 43:369–374 (1994).

Jacobs et al., "Metabolic Effects of IGF–I and Insulin in Spontaneously Diabetic BB/w Rats" *Am. J. Physiol.* 260:E262–E268 (1991).

Kerr et al., "Effect of Insulin–like growth Factor 1 on the Responses to and Recognition of Hypoglycemia" *Diabetes: American Diabets Association (ADA), San Antonio, Texas, Jun. 20–23, 1992* (abstract #225), 52nd Annual Meeting edition 41(suppl):60A (Jun. 1992).

Kerr et al., "Effect of Insulin–like Growth Factor–1 on the Responses to and Recognition of Hypoglycemi in Humans" *J. Clin. Invest.* 91:141–147 (1993).

Kissel et al., "Applikationsformen des Insulins (Forms of Administration of Insulin—English translation provided)" *Deutsche Apotheker–Zeitung (Germany)* 134(7):25–39 (1994).

Kuzuya et al., "Trial of insulinlike growth factor I therapy for patients with extreme insulin resistance syndromes" *Diabetes* 42:696–705 (1993).

Leahy et al., "Insulin–Like Growth Factor–I at Physiological Concentrations is a Potent Inhibitor of Insulin Secretion" *Endocrinology* 126(3):1593–1598 (1990).

Lewitt et al., "Insulin–like Growth Factor–binding Protein–1 Modulates Blood Glucose Levels" *Endocrinology* 129(4):2254–2256 (1991).

Lieberman et al., "Effects of recombinant human insulin–like growth factor–I (rhIGF–I) on total and fre IGF–I concentrations, IGF–binding proteins, and glycemic response in humans" *J. Clin. Endocrinol. and Metabl.* 75(1):30–36 (1992).

Mathe, G., "Relations of hormones and growth factors at the crossroad of pathogenesis and pharmacotherapeutics. The case of diabetes mellitus" *Biomedicine & Pharmacotherapy* 49(5):221–224 (1995).

Mauk and Mauk, "Interaction between cytochrome $b_5$ and human methemoglobin" *Biochemistry* 21(19):4730–473 (Sep. 14, 1982).

Morrow et al., "Recombinant Human (rh) IGF–1 Reverses Hyperglycemia and Improves Insulin Sensitivity in Severe Insulin Resistance" *Diabetes–53rd Annual Meeting, Jun. 12–15, 1993* (abstract No. 269) 42:83A (Suppl. 1 1993).

"Quick inventory check: diabetes products" *U.S. Pharmacist* 18 (Nov. Suppl.):38–40 (1993).

Quin et al., "Acute Response to Recombinant Insulin–like Growth Factor I in a Patient with Mendenhall's Syndrome" *New England J. of Medicine* 323:1425–1426 (1990).

Randazzo et al., "Characterization of the Growth of Murine Fibroblasts That Express Human Insulin Receptors" *Exp. Cell Res.* 190(1):31–39 (1990).

Rinderknecht and Humbel, "Polypeptides with nonsuppressible insulin–like and cell–growth promoting activities in human serum: isolation, chemical characterization, and some biological properties of form I and II" *Proc. Natl. Acad. Sci USA* 73(7):2365–2369 (1976).

Rinderknecht and Humbel, "The amino acid sequence of human insulin–like growth factor I and its structural homology with proinsulin" *Journal of Biological Chemistry* 253(8):2769–2776 (1978).

Ross et al., "The Role of Insulin, Growth Hormone and IGF–I as Anabolic Agents in the Critically I11" *Intensive Care Med.* 19(2):S54–S57 (Suppl. 1993).

Saad et al., "Low–doses of Insulin–like Growth Factor–I Improve Insulin Sensitivity" *Diabetologia* (Abstract 152) 37:A40 (Supp. 1 1994).

Schlach et al., "Short–Term Effects of Recombinant Human Insulin–Like Growth Factor I on Metabolic Control of Patients with Type II Diabetes Mellitus" *J. of Clinical Endocrinology & Metabolism* 77(6):1563–1568 (1993).

Schalch et al., "Short–Term metabolic effects of recombinant human insulin–like growth factor I (rhIGF–I) in type II diabetes mellitus" *Modern Concepts of Insulin–Like Growth Factors,* Spencer, ed., New York:Elsevier Science Publ. Co. pp. 705–713 (1991).

Schoenle et al., "Recombinant human insulin–like growth factor I(rhIGF I) reduces hyperglycaemia in patients with extreme insulin resistance" *Diabetologia* 34:675–679 (1991).

Sherwin et al., "Metabolic Effects of Insulin–like Growth Factor I in Normal Humans" *Horm. Res.* 41:97–101 (Suppl. 2 1994).

Shojaee–Moradie et al., "A Comparison of the Effects of Insulin–like Growth Factor–I, Insulin and Combined Infusions of Insulin and Insulin–like Growth Factor–I on Glucose Metabolism in Dogs" *European Journal of Clinical Investigation (United Kingdom)* 25(12):920–928 (1995).

Sieradzki et al., "Stimulatory Effect of Insulin–Like Growth Factor–I on [3H]thymidine Incorporation, DNA Content and Insulin Biosynthesis and Secretion of Isolated Pancreatic Rat Islets" *J. of Endocrinology* 117(1):59–62 (1988).

Srinivasan et al., "Iontophoresis of polypeptides: effect of ethanol pretreatment of human skin" *Journal of Pharmaceutical Sciences* 79(7):588–591 (Jul. 1990).

Takano et al., "Effects of sc Administration of Recombinant Human Insulin–like Growth Factor I (IGF–I) on Normal Human Subjects" *Endocrinol. Japan* 37(2):309–317 (1990).

Tanner et al., "Comparative rapditiy of response of height, limb muscle and limb fat to treatment with human growth hormone in patients with and without growth hormone deficiency" *Acta Endocrinologica* 84:681–696 (1977).

Tomas et al., "Cojoint IGF–I and Insulin Infusion Shows Diverse Interactive Effects in Diabetic Rats" *Diabetes* 45:170–177 (1996).

Umpleby et al., "Effects of Insulin–like Growth Factor–I (IGF–I), Insulin and Combined IGF–I–insulin Infusions on Protein Metabolism in Dogs" *Eur. J. Clin. Invest.* 24:337–344 (1994).

Underwood et al., "Regulation of somatomedin–c/insulin–like growth factor I by nutrients" *Hormone Res.* 24:166–176 (1986).

Usala et al., "Brief report: treatment of insulin–resistant diabetic ketoacidosis with insulin–like growth factor I in an adolescent with insulin–dependent diabetes" *New England J. of Medicine* 327(12):853–857 (1992).

Uthne et al., "Effects of human somatomedin preparations on membrane transport and protein synthesis in the isolated rat diaphragm" *J. Clin. Endocrinol. Metab.* 39(3):548–554 (1974).

Van Schravendijk et al., "Direct Effect of Insulin and Insulin–Like Growth Factor–I on the Secretory Activity of Rat Pancreatic Beta Cells" *Diabetologia* 33(11):649–653 (1990).

Van Wyk et al., "The somatomedins: a family of insulinlike hormones under growth hormone control" *Recent Prog. Horm. Res.* 30:259–318 (1974).

Valchopapadopoulou et al., "Metabolic and Clinical Response to Recombinant Human Insulin–like Growth Factor I in Myotonic Dystrophy—A Clinical Research Center Study" *J. Clin. Endo. Metabl.* 80(12):3715–3723 (1995).

Wilton et al., "Treatment with recombinant human insulin–like growth factor I of children with growth hormone receptor deficiency (Laron syndrome)" *Acta Paediatr Suppl.* 383:137–142 (1992).

Zenobi et al., "Effects of insulin–like growth factor–I on glucose tolerance, insulin levels, and insulin secretion" *J. Clin. Invest.* 89:1908–1913 (1992).

Zenobi et al., "Insulin–like growth factor–I improves glucose and lipid metabolism in type 2 diabetes mellitus" *J. Clin. Invest.* 90:2234–2241 (1992).

\* cited by examiner

FORMULATED COMPOSITION

This application claims the benefit of Provisional Application No. 60/128,392, filed Apr. 8, 1999.

BACKGROUND OF THE INVENTION

1. Field of the Invention

This invention relates to formulations containing mixtures of oppositely-charged polypeptides such as insulin-like growth factor (IGF-I) and insulin. In particular, this invention entails a formulation containing selected excipients that enable the mixing of oppositely-charged proteins in the same formulation, the excipients preventing the interaction of the proteins that normally would make them precipitate from the solution.

2. Description of Related Art

Human IGF-I is a 7649-dalton polypeptide (Rinderknecht and Humbel, *Proc. Natl. Acad. Sci. USA*, 73: 2365 (1976); Rinderknecht and Humbel, *J. Biol. Chem.*, 253: 2769 (1978)) belonging to a family of somatomedins with insulin-like and mitogenic biological activities that modulate the action of growth hormone (GH). Van Wyk et al., *Recent Prog. Horm. Res.*, 30: 259 (1974); Binoux, *Ann. Endocrinol.*, 41: 157 (1980); Clemmons and Van Wyk, *Handbook Exp. Pharmacol.*, 57: 161 (1981); Baxter, *Adv. Clin. Chem.*, 25: 49 (1986); U.S. Pat. No. 4,988,675; WO 91/03253; and WO 93/23071. IGF-I contains three disulfide bonds, and has a pI of 8.65 and molar absorptivity of 0.645 at 276 nm. IGF-I naturally occurs in human body fluids, for example, blood and human cerebral spinal fluid. Most tissues and especially the liver produce IGF-I together with specific IGF-binding proteins. Like GH, IGF-I is a potent anabolic protein. See Tanner et al., *Acta Endocrinol.*, 84: 681–696 (1977); Uthne et al., *J. Clin. Endocrinol. Metab.*, 39: 548–554 (1974). See also Ross et al., *Intensive Care Med.*, 19 Suppl. 2: S54–57 (1993), which is a review of the role of insulin, growth hormone, and IGF-I as anabolic agents in the critically ill.

IGF-I may be purified from natural sources, e.g., human serum (Rinderknecht and Humbel, *J. Biol. Chem.*, supra), or made recombinantly (e.g., EP 123,228 and 128,733). Various methods for formulating IGF-I have been described. These include, for example, EP 440,989, which discloses a method for preparing a dried composition of IGF-I, which comprises drying a solution containing IGF-I together with a strong acid, WO 91/18621 on formulating IGF-I in a citrate buffer at pH 6, U.S. Pat. No. 5,374,620 on formulating IGF-I and GH in a growth-promoting composition, U.S. Pat. No. 5,681,814 on formulating IGF-I in an acetate buffer, WO 94/15584 on a stable solution containing IGF-I in a phosphate buffer in an amount of 50 mmol or less, giving a pH of 5.5 to 6.5, which is isotonic and suitable for injection, and WO 95/34318 on a solution comprising IGF-I in an aqueous solution with a reduced concentration of oxygen.

IGF-I has hypoglycemic effects in humans similar to insulin when administered by intravenous bolus injection, but also promotes positive nitrogen balance. Underwood et al., *Hormone Research*, 24: 166 (1986). IGF-I is known to exert glucose-lowering effects in both normal (Guler et al., *N. Engl. J. Med.*, 317: 137–140 (1987)) and diabetic individuals (Schoenle et al., *Diabetologia*, 34: 675–679 (1991); Zenobi et al., *J. Clin. Invest.*, 90: 2234–2241 (1992)) (see also Sherwin et al., *Hormone Research*, 41 (Suppl. 2): 97–101 (1994); Takano et al., *Endocrinol. Japan*, 37: 309–317 (1990); Guler et al., *Acta Paediatr. Scand.* (*Suppl.*), 367: 52–54 (1990)), with a time course described as resembling Regular insulin. See also Kerr et al., "Effect of Insulin-like Growth Factor 1 on the responses to and recognition of hypoglycemia," American Diabetes Association (ADA), 52nd Annual Meeting, San Antonio, Tex., Jun. 20–23, 1992, which reported an increased hypoglycemia awareness following rhIGF-I administration. In addition, single administration of rhIGF-I reduces overnight GH levels and insulin requirements in adolescents with IDDM. Cheetham et al., *Clin. Endocrinol.*, 40: 515–522 (1994); Cheetham et al., *Diabetologia*, 36: 678–681 (1993).

Recombinant human IGF-I administered to Type II diabetics as reported by Schalch et al., *J. Clin. Endocrinol. Metab.*, 77: 1563–1568 (1993) demonstrated a fall in both serum insulin as well as a paralleled decrease in C peptide levels which indicated a reduction in pancreatic insulin secretion after five days of IGF-I treatment. This effect has been independently confirmed by Froesch et al., *Horm. Res.*, 42: 66–71 (1994). In vivo studies in normal rats also illustrate that IGF-I infusion inhibits pancreatic insulin release. Furnsinn et al., *Endocrinology*, 135: 2144–2149 (1994). In addition, in pancreas perfusion preparations IGF-I also suppresses insulin secretion. Leahy et al., *Endocrinology*, 126: 1593–1598 (1990). Despite these clear in vivo inhibitory effects of IGF-I on insulin secretion in humans and animals, in vitro studies have not yielded such uniform results.

In vitro studies using multiple concentrations of both IGF-I and glucose have shown various degrees of inhibition of insulin secretion, e.g., from no effect (Sieradzki et al., *J. Endocrinol.*, 117: 59–62 (1988)) to a 30% decrease in insulin release utilizing physiological levels of IGF-I. Van Schravendijk et al., *Diabetologia*, 33: 649–653 (1990). In a recent study using human pancreatic islets, Eizirik et al., *Eur. J. Endocr.*, 133: 248–250 (1995) found no effect of IGF-I on medium insulin accumulation or on glucose-stimulated insulin release. The investigators speculate that the effect of IGF-I seen in vivo on insulin secretion may be secondary to the extra-pancreatic effects of IGF-I rather than its direct effects on the pancreas. Therefore, the mode and site of action of IGF-I on insulin secretion are not fully understood.

A number of biochemical changes induced by short-term rhIGF-I administration are described in the literature. Prominent among these is a phosphate- and potassium-lowering effect of recombinant human IGF-I (rhIGF-I) reported in healthy subjects during euglycemic clamp. Boulware et al., "Phosphate and potassium lowering effects of insulin-like growth factor I in humans: comparison with insulin" The Endocrine Society, 74th Annual Meeting, San Antonio, Tex., 1992 June 24–27 See also Guler et al., *Acta Paediatr. Scand.* (*suppl.*), 367, supra.

Recombinant human IGF-I (rhIGF-I) has the ability to improve insulin sensitivity. For example, rhIGF-I (70 μg/kg bid) improved insulin sensitivity in non-diabetic, insulin-resistant patients with myotonic dystrophy. Vlachopapadopoulou et al., *J. Clin. Endo. Metab.*, 80: 3715–3723 (1995). Saad et al., *Diabetologia*, 37. Abstract 40 (1994) reported dose-dependent improvements in insulin sensitivity in adults with obesity and impaired glucose tolerance following 15 days of rhIGF-I treatment (25 μg and 100 μg/kg bid). RhIGF-I also improved insulin sensitivity and glycemic control in some patients with severe type A insulin resistance (Schoenle et al., *Diabetologia*, 34: 675–679 (1991); Morrow et al., *Diabetes*, 42 (Suppl.): 269 (1993) (abstract); Kuzuya et al., *Diabetes*, 42: 696–705 (1993)) or others with non-insulin dependent diabetes mellitus. Schalch et al., "Short-term metabolic effects of recombinant human insulin-like growth factor I (rhIGF-I) in type II diabetes mellitus", in: Spencer EM, ed., *Modern Concepts of Insulin-like Growth Factors* (New York: Elsevier: 1991) pp. 705–713; Zenobi et al., *J. Clin. Invest.*, 90: 2234–2241 (1992).

Though insulin resistance has not been considered a prominent feature of type I diabetes, it is clearly present in some individuals and may be most clinically important during adolescence. As GH has well-known anti-insulin effects, the elevated GH levels during adolescence may mediate much of this insulin resistance. Press et al., supra; Defeo et al., supra; Campbell et al., *N. Eng. J. Med.*, supra, Campbell et al., *Metabolism*, supra; Arias et al., supra; Davidson et al., supra.

A general scheme for the etiology of some clinical phenotypes that give rise to insulin resistance and the possible effects of administration of IGF-I on selected representative subjects are given in several references. See, e.g., Elahi et al., "Hemodynamic and metabolic responses to human insulin-like growth factor-1 (IGF-I) in men," in: *Modern Concepts of Insulin-Like Growth Factors*, (Spencer, E M, ed.), Elsevier, N.Y., pp. 219–224 (1991); Quin et al., *New Engl. J. Med.*, 323: 1425–1426 (1990); Schalch et al., "Short-term metabolic effects of recombinant human insulin-like growth factor 1 (rhIGF-I) in type II diabetes mellitus," in: *Modern Concepts of Insulin-Like Growth Factors*, (Spencer, E M, ed.), Elsevier, N.Y., pp. 705–713 (1991); Schoenle et al., *Diabetologia*, 34: 675–679 (1991); Usala et al., *N. Eng. J. Med.*, 327: 853–857 (1992); Lieberman et al., *J. Clin. Endo. Metab.*, 75: 30–36 (1992); Zenobi et al., *J. Clin. Invest.*, 90: 2234–2241 (1992); Zenobi et al., *J. Clin. Invest.*, 89: 1908–1913 (1992); Kerr et al., *J. Clin. Invest.*, 91: 141–147 (1993). WO 94/16722 discloses a method of chronic modification of cell barrier properties by exposing a cell to a modification-effective amount of IGF-I for at least about seven days and a method of chronic amelioration or reversal of insulin resistance. However, when IGF-I was used to treat type II diabetes patients in the clinic at a dose of 120–160 μg/kg twice daily, the side effects outweighed the benefit of the treatment. Jabri et al., *Diabetes*, 43: 369–374 (1994). See also Wilton, *Acta Paediatr.*, 383: 137–141 (1992) regarding side effects observed upon treatment of patients with IGF-I.

U.S. Pat. No. 4,988,675 describes treatment of type II diabetics with IGF-I, U.S. Pat. No. 5,466,670 describes treatment of type I diabetics with IGF-I, WO 91/03253 reports use of IGF-I to treat severe insulin-resistant diabetics, and WO 96/01124 describes use of IGF-I to prevent diabetes, delay clinical onset of diabetes, and provide a protective effect against diabetes.

The treatments of choice in type II diabetes have become combination therapies. These combinations historically involved the use of multiple forms of insulin, short-acting insulin, intermediate-acting, and long-acting insulins. Review articles on insulin formulations include Kissel and Volland, *Deutsche Apotheker-Zeitunp*, 134: 25 (1994) and Campbell, *Pharmcy Times*. 59: 40 (1993). More recently, combinations of insulin with other anti-diabetic drugs, which are taken orally such as sulphonylureas and biguanides, have become commonplace.

As to combinations of IGF and insulin, Gunn et al., *Biochem. Arch.*, 5: 53–59 (1989) discloses the anabolic effect of insulin and IGF-II. Jacob et al., *Am. J. Physiol.*, 260: E262–E268 (1991) discloses the metabolic effects of IGF-I and insulin in spontaneously diabetic BB/w rats; see also U.S. Pat. No. 4,876,242. Furthermore, the stimulation of cardiac protein synthesis after treatment with insulin and IGF is disclosed by Fuller et al., *Biochem. Soc. Trans.*, 19: 277S (1991). The experiments have been performed in vitro with freshly isolated cardiac myocytes. The effects on protein metabolism after treatment with insulin and IGF on dogs that have been starved overnight are reported by Umpleby et al., *Eur. J. Clin. Invest.*, 24: 337–344 (1994). Shojaee-Moradie et al., *J. Clin. Invest.*, 25: 920–928 (1995) discloses a comparison of the effects of IGF-I, insulin, and combined infusions thereof on glucose metabolism in dogs. Randazzo and Jarett, *Exp. Cell Res.*, 190 (1): 31–39 (1990) discloses characterization of the growth of murine fibroblasts that express human insulin receptors and the effect of IGF-I and insulin on DNA synthesis thereof. Tomas et al., *Diabetes*, 45: 170–177 (1996) discloses the effects of joint IGF-I and insulin infusion on diabetic rats. Dunger et al., *Metabolism*, 44: 119–123 (1995) suggests that IGF-I in conjunction with insulin may provide an additional approach to management of IDDM during adolescence. Mathe, *Biomedicine and Pharmacotherapy*, 49: 221–224 (1995) discloses the role of IGF's in their relation with insulin for treating diabetes mellitus.

As to the patent literature, U.S. Pat. No. 4,988,675 discloses a combination of IGF-I with a lower amount of insulin than normal to treat Type II diabetes. WO 96/01125 published Jan. 18, 1996 discloses the use of a combination of insulin and an IGF-I in the manufacture of a medicament for counteracting a decrease in nitrogen balance and for counteracting a decrease in protein synthesis and that can be used for treatment of a protein catabolism due to glucocorticoid excess. U.S. Pat. No. 5,091,173 discloses a composition suitable for topical application to mammalian skin or hair comprising a cell-free supernatant from a culture of dermal papilla cells sufficient to increase hair growth comprising one or more members of the IGF family selected from IGF-I, IGF-II, and insulin.

There are various forms of human insulin on the market that differ in the duration of action and onset of action. Jens Brange, *Galenics of Insulin, The Physico-chemical and Pharmaceutical Aspects of Insulin and Insulin Preparations* (Springer-Verlag, New York, 1987), page 17–40. Regular insulin is a clear neutral solution that contains hexameric insulin. It is short acting, its onset of action occurs in 0.5 hour after injection, and duration of action is about 6–8 hours. NPH (Neutral Protamine Hagedorn)-insulin, also called Isophane Insulin, is a crystal suspension of insulin-protamine complex. These crystals contain approximately 0.9 molecules of protamine and two zinc atoms per insulin hexamer. Dodd et al., *Pharmaceutical Research*, 12: 60–68 (1995). NPH-insulin is an intermediate-acting insulin; its onset of action occurs in 1.5 hours and its duration of action is 18–26 hours. 70/30 insulin is composed of 70% NPH-insulin and 30% Regular insulin. There are also Semilente insulin (amorphous precipitate of zinc insulin complex), UltraLente insulin (zinc insulin crystal suspension), and Lente insulin (a 3:7 mixture of amorphous and crystalline insulin particles), as well as HUMALOG® insulin lispro injection (rDNA origin) rapid-acting monomeric insulin solution, as a result of reversing the Lys (B28) and Pro(B29) amino acids on the insulin B-chain) that was recently introduced into the market by Eli Lilly and Company.

NPH-, 70/30, and Regular insulin are the most widely used insulins, accounting for 36%, 28%, and 15%, respectively, of the insulin prescriptions in 1996. These three forms of insulin add up to 79% of all insulin prescriptions. It was therefore determined that the IGF-I formulation needs to be mixable with Regular, NPH-, and 70/30 insulin.

Patients with Type I or Type II diabetes typically take two to four subcutaneous injections of insulin daily to control their blood sugar. The use of an injectable drug other than insulin to treat diabetes, such as IGF-I, is naturally limited due to the desire of diabetics to administer a minimum number of injections. Adding two more subcutaneous injections daily, for IGF-I administration, to regimens that already require several injections per day of insulin is not practical. Further, when combining two proteins such as IGF-I and insulin, it would be necessary to have the resulting formulation stable and well absorbed by the patient, as well as having intermediate-acting insulin. An intermediate-acting insulin regulated in a time- and target-tissue-dependent manner in response to changing demands of the metabolic environment is described by Lewitt et al., *Endocrinology*, 129: 2254–2256 (1991).

U.S. Pat. No. 5,788,959 discloses a drug-delivery device comprising a single-phase matrix solution of oppositely-charged water-soluble polymers such as polypeptides wherein the matrix solution has dispersed therein a pharmaceutically active ingredient different from the polymers. Further, Burgess et al., *J. Pharm. Pharmacol.*, 43: 232–236 (1991) discloses complex coacervation between oppositely-charged albumin and acacia mixtures, with coacervation being a common method of microencapsulation. Mauk and Mauk, *Biochemistry*, 21: 4730–4734 (1982) discloses complex formation between purified human methemoglobin and the tryptic fragment of bovine liver cytochrome $b_5$ and report a model for interaction between these molecules in which each hemoglobin subunit binds one cytochrome $b_5$ by means of complementary charge interactions between oppositely-charged groups on the two proteins. Furthermore, EP 615,444 discloses a peroral administration form for peptidic medicaments containing the medicament, such as insulin, distributed in a gelatin or gelatin derivative matrix of opposite charge. EP 313,343 discloses a method of purifying a crude protein from its impurities by ion-exchange chromatography at a pH such that the protein and impurities have an opposite charge so that selective binding occurs.

Presently, diabetics mix NPH-insulin (intermediate-acting neutral protamine hagedorn insulin) with Regular insulin. It would be desirable to mix oppositely-charged polypeptides such as insulin and IGF-I, each from separate vials in the same syringe or other delivery vessel, and to inject or otherwise deliver the mixture immediately. U.S. Pat. No. 5,783,556 discloses a formulation of mixed NPH-insulin and IGF-I. U.S. Pat. No. 5,756,463 discloses a combination of IGF-I and insulin and its use in counteracting a decrease in nitrogen balance and a decrease in protein synthesis. U.S. Pat. No. 4,608,364 discloses an active-compound combination of an insulin derivative and an unmodified insulin or a specific analog thereof for treating diabetes. It would be desirable to mix all types of insulin with IGF-I for this purpose, as well as to mix other polypeptides such as protamine and insulin, which are currently sold as a precipitating complex.

SUMMARY OF THE INVENTION

Upon mixing, two polypeptides that are oppositely charged tend to associate with each other and form an aggregate or precipitate out of solution. Use of certain formulation excipients can prevent aggregation and precipitation of such polypeptides when mixed, including IGF-I with insulin and protamine with insulin. Many excipients such as salts, buffers, neutral amino acids, polyols, sugars, and detergents were not effective in preventing precipitation.

Accordingly, the present invention provides, in one embodiment, a composition comprising a mixture of pharmaceutically-active polypeptides of opposite charge and an excipient selected from the group consisting of arginine, lysine, glutamate (glutamic acid), sodium dodecyl sulfate, and a combination of beta-hydroxy cyclodextrin and arginine, wherein the polypeptides are soluble in the composition.

In a preferred aspect of this embodiment, the composition may further comprise a buffer such as histidine, at a pH of about 7 to 7.5.

In a further embodiment, the invention provides a kit comprising:
 (a) a container comprising the above composition comprising effective amounts of the polypeptides; and
 (b) instructions for using the above composition to treat a disorder against which the composition is effective.

If the polypeptides are IGF-I and an insulin, the disorder is preferably a hyperglycemic disorder.

In yet another aspect, the invention supplies a method for preparing the above composition comprising mixing together as component (a) a first polypeptide in an excipient selected from the group consisting of arginine, lysine, glutamic acid, sodium dodecyl sulfate, beta-hydroxy cyclodextrin, and beta-cyclodextrin sulfobutyl ether; and as component (b) a second polypeptide having an opposite charge from the first polypeptide.

In a preferred aspect, the method may further comprise the step of incubating the mixture for a period of time at about 30–40° C., preferably for about 15 minutes at 37° C., wherein the composition further comprises phosph buffered saline. In still another embodiment, the invention provides a kit for preparing the above composition comprising:
 (a) a container comprising a first polypeptide in an excipient selected from the group consisting of arginine, lysine, glutamic acid, sodium dodecyl sulfate, and a combination of beta-hydroxy cyclodextrin and arginine;
 (b) a container comprising a second polypeptide having an opposite charge from the first polypeptide; and
 (c) instructions for combining the contents of containers (a) and (b).

Preferably, the resulting mixture is a pharmaceutically acceptable formulation.

In a still further aspect, the invention provides a method for treating a hyperglycemic disorder such as diabetes in a mammal comprising administering to the mammal, preferably by either injection or infusion, an effective amount of the above composition.

Mixing of two polypeptides of opposite charge such as IGF-I and an insulin requires the physical and chemical properties of both polypeptides to remain unchanged after mixing. Further, it is preferred that the pharmacokinetic and glucose pharmacodynamic profiles remain the same before and after mixing. If one of the polypeptides is IGF-I, it is preferred that the formulation have a minimum of a two-year shelf life. To enable mixing with another polypeptide, the formulation of the first polypeptide can be a clear liquid formulation, or a suspension formulation in which the polypeptide (such as IGF-I) is in the form of crystals, amorphous precipitate, or proteindry powder. An Example herein describes the development of a clear liquid IGF-I formulation that is mixable with insulin.

If the polypeptides are IGF-I and insulin, the targeted IGF-I dose will be 10, 20 or 40 µg/kg/injection (or 1, 2 or 4 µl/kg/injection for a 10 mg/ml IGF-I formulation). From the insulin dosage used by Type I and Type II patients in phase II clinical trials, it can be calculated that the maximum potential mixing ratio can reach 6:1 (vol:vol) for Regular insulin:IGF-I. The minimum potential mixing ratio can reach 1:15 (vol:vol) for NPH-insulin:IGF-I. Therefore, in the Example herein, mixing ratios ranging from 1:6 to 6:1 (vol:vol) were studied for mixing Regular insulin with IGF-I; mixing ratios ranging from 1:15 to 15:1 (vol:vol) were studied for mixing NPH-insulin with IGF-I; and mixing ratios ranging from 1:15 to 6:1 (vol:vol) were studied for mixing 70/30 insulin with IGF-I.

DESCRIPTION OF THE PREFERRED EMBODIMENTS

A. Definitions

Figure 1:
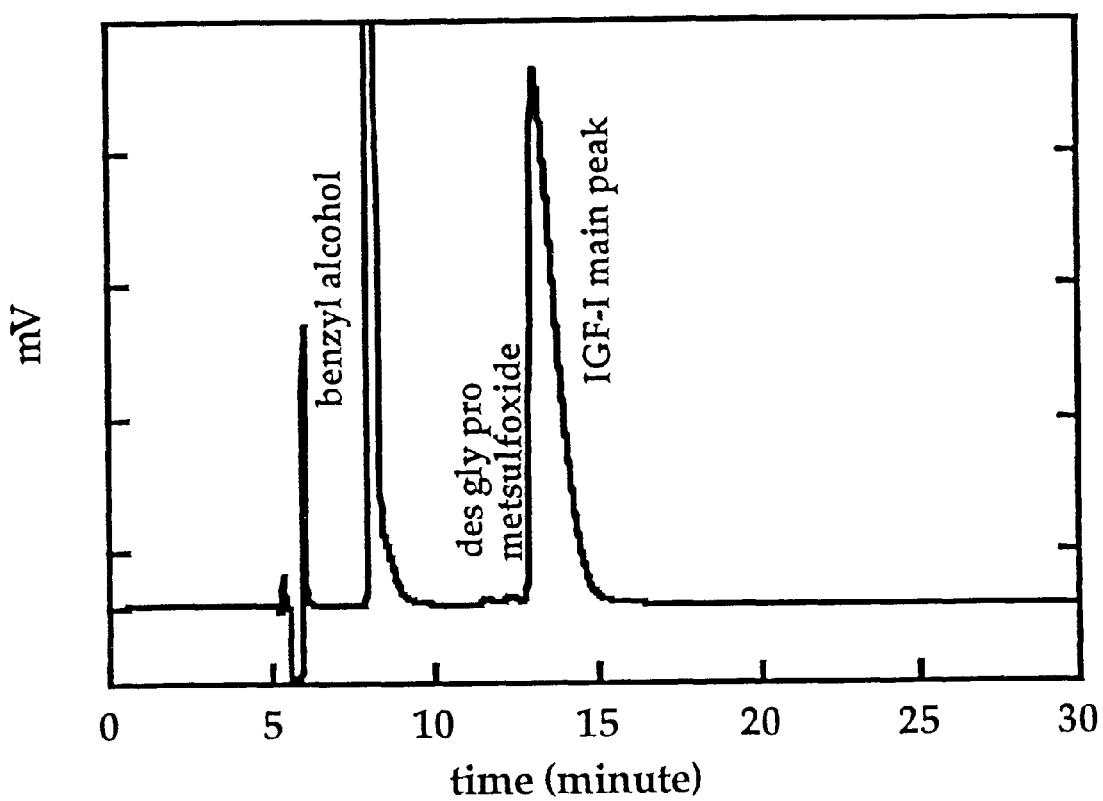
FIG. 1 shows the acidic pH reversed-phase HPLC chromatogram of an IGF-I sample.

As used herein "polypeptide" or "polypeptide of interest" refers generally to peptides and proteins having more than about ten amino acids. Examples of mammalian polypeptides include molecules such as, e.g., renin, a growth hormone, including human growth hormone; bovine growth hormone; growth hormone releasing factor; parathyroid hormone; thyroid stimulating hormone; lipoproteins; α1-antitrypsin; insulin A-chain; insulin B-chain; proinsulin; thrombopoietin; follicle stimulating hormone; calcitonin; luteinizing hormone; glucagon; clotting factors such as factor VIIIC, factor IX, tissue factor, and von Willebrands factor; anti-clotting factors such as Protein C; atrial naturietic factor; lung surfactant; a plasminogen activator, such as urokinase or human urine or tissue-type plasminogen activator (t-PA); bombesin; thrombin; hemopoietic growth factor; tumor necrosis factor-alpha and -beta; enkephalinase; a serum albumin such as human serum albumin; mullerian-inhibiting substance; relaxin A-chain; relaxin B-chain; prorelaxin; mouse gonadotropin-associated peptide; a microbial protein, such as beta-lactamase; DNase; inhibin; activin; vascular endothelial growth factor (VEGF); receptors for hormones or growth factors; integrnn; protein A or D; rheumatoid factors; a neurotrophic factor such as brain-derived neurotrophic factor (BDNF), neurotrophin-3, -4, -5, or -6 (NT-3, NT-4, NT-5, or NT-6), or a nerve growth factor such as NGF (cardiac hypertrophy factor) such as cardiotrophin-1 (CT-1); platelet-derived growth factor (PDGF); fibroblastgrowth factor such as aFGF and bFGF; epidermal growth factor (EGF); transforming growth factor (TGF) such as TGF-alpha and TGF-beta, including TGF-β1, TGF-β2, TGF-β3, TGF-β4, or TGF-β5; insulin-like growth factor-I and -II (IGF-I and IGF-II); des(1–3)-IGF-I (brain IGF-I), insulin-like growth factor binding proteins; CD proteins such as CD-3, CD-4, CD-8, and CD-19; erythropoietin; osteoinductive factors; immunotoxins; a bone morphogenetic protein (BMP); protamine; an interferon such as interferon-alpha, -beta, and -gamma; colony stimulating factors (CSFs), e.g., M-CSF, GM-CSF, and G-CSF; interleukins (ILs), e.g., IL-1 to IL-10; anti-HER-2 antibody; superoxide dismutase; T-cell receptors; surface membrane proteins; decay accelerating factor; viral antigen such as, for example, a portion of the AIDS envelope; transport proteins; homing receptors; addressins; regulatory protcins; antibodies; and fragments of any of the above-listed polypeptides.

The preferred polypeptides of interest are mammalian polypeptides, most preferably human polypeptides. Examples of such mammalian polypeptides include t-PA, VEGF, gp120, anti-HER-2, anti-CD 11a, anti-CD 18, DNase, IGF-I, IGF-II, insulin, protamine, brain IGF-I, growth hormone, relax in chains, LHRH analogues, cholecystokinin-8 analogues, growth hormone releasing factor, insulin chains or pro-insulin, urokinase, immunotoxins, neurotrophins, and antigens. Especially preferred mammalian polypeptides are those combinations that are administered to mammals sufficiently frequently that it would be desirable to give one shot or dosage containing both. Particularly preferred such combinations include, e.g., insulin and an IGF, most preferably IGF-I, or protamine and insulin, or growth hormone and an IGF such as IGF-I, or a LHRH analogue such as leuprolide and a cholecystokinin-8 analogue such as CCK-8.

As used herein, "oppositely-charged polypeptides" or "polypeptides of opposite charge" means that one polypeptide is negatively charged and one is positively charged at a given pH. The charges can be determined, for example, based on $pK_a$ values of the ionizable groups of the polypeptide, or by its isoelectric point (pI), as determined, for example, by gel electrofocusing. Generally, the negatively-charged polypeptide has a net negative charge at about pH 6 to 8, or has more than about five negatively-charged residues. For a polypeptide to be used as a negatively-charged polypeptide, it must have a higher number of negative charges compared to the number of positive charges. Conversely, the positively-charged polypeptide generally has a net positive charge at about pH 6 to 8 or has more than about five positively-charged residues. For a polypeptide to be used as a positively-charged polypeptide, it must have a higher number of positive charges compared to the number of negative charges. For example, IGF-I and insulin have pI values of 8.7 and 5.4, respectively, at a solution pH of 7.2, and therefore are oppositely charged. Further, at solution pH 7.4, leuprolide (a LHRH analogue) is positively charged, whereas a cholecystokinin-8 analogue (CCK-8) is negatively charged due to a pI value of less than 4. The charges on the two oppositely-charged polymers are sufficient to bring about an electrostatic interaction. Other examples of negatively-charged polypeptides include heparin, albumin (bovine serum albumin has a pI of 4.8, with a net negative charge of ~18 at pH 7.1), and beta-lactoglobulin (pI of 5.1 with a net negative charge of −5 at pH 7.1).

Oppositely-charged polypeptides herein may be native polypeptides or those that are derivatized or synthetic, providing that they are "pharmaceutically active." By "pharmaceutically active" is meant a polypeptide that has efficacy in one or more biological assays, including immunological assays and mitogenic assays. For example, pharmaceutically active polypeptides include antigens as well as antibodies, and receptors as well as ligands, which act in an immunological or biological sense.

As used herein, "IGF-I" refers to insulin-like growth factor from any species, including bovine, ovine, porcine, equine, and preferably human, in native-sequence or in variant form, and from any source, whether natural, synthetic, or recombinant. Preferred herein for animal use is that form of IGF-I from the particular species being treated, such as porcine IGF-I to treat pigs, ovine IGF-I to treat sheep, bovine IGF-I to treat cattle, etc. Preferred herein for human use is human native-sequence, mature IGF-I, more preferably without a N-terminal methionine, prepared, e.g., by the process described in EP 230,869 published Aug. 5, 1987; EP 128,733 published Dec. 19, 1984; or EP 288,451 published Oct. 26, 1988. More preferably, this native-sequence IGF-I is recombinantly produced and is available from Genentech, Inc., South San Francisco, Cailf. for clinical investigations.

The preferred IGF-I variants are those described in U.S. Pat. Nos. 5,077,276; 5,164,370; or 5,470,828; or in WO 87/01038, i.e., those wherein at least the glutamic acid residue is absent at position 3 from the N-terminus of the mature molecule or those having a deletion of up to five amino acids at the N-terminus. The most preferred variant has the first three amino acids from the N-terminus deleted (variously designated as brain IGF, tIGF-I, des(1–3)-IGF-I, or des-IGF-I).

As used herein, "insulin" refers to f insulin from any species, including bovine, ovine, porcine, equine, and preferably human, and from any source, whether natural, synthetic, or recombinant. All insulin drugs reported, for example, in *Diabetes Mellitus—Theory and Practice*, fourth edition, Harold Rifkin, MD, Ed. (Elsevier, N.Y., 1990), Chapter 29, and *U.S. Pharmacist*, 18 (November Suppl.) p. 38–40 (1993) are suitable herein. All the various forms of human insulin on the market are included, such as those mentioned in Jens Brange, *Galenics of Insulin, The Physicochemical and Pharmaceutical Aspects of Insulin and Insulin Preparations* (springer-Verlag, New York, 1987), page 17–40. These include Regular insulin, NPH (Neutral Protamine Hagedorn) -insulin, also called Isophane Insulin, 70/30 insulin, composed of 70% NPH-insulin and 30% Regular insulin, Semilente insulin, UltraLente insulin, Lente insulin, and HUMALOG® insulin lispro injection (rDNA origin). Preferred herein for animal use is that form of insulin from the particular species being treated, such as human insulin to treat humans.

As used herein, the term "disorder" in general refers to any condition that would benefit from treatment with the oppositely-charged polypeptides in the composition herein, including any disease or disorder that can be treated by effective amounts of these polypeptides. This includes chronic and acute disorders, as well as those pathological conditions that predispose the mammal to the disorder in question. Non-limiting examples of disorders to be treated herein include benign and malignant tumors; leukemias and lymphoid malignancies; neuronal, glial, astrocytal, hypothalamic and other glandular, macrophagal, epithelial, stromal, and blastocoelic disorders; hematopoiesis-related disorders; tissue-growth disorders; skin disorders; desmoplasia, fibrotic lesions; hyperglycemic disorders; kidney disorders; bone-related disorders; trauma such as burns, incisions, and other wounds; catabolic states; testicular-related disorders; and inflammatory, angiogenic, and immunologic disorders, including arteriosclerosis. An example of a disorder that can benefit from treatment with IGF-I and an insulin includes diabetes.

As used herein, the term "hyperglycemic disorders" refers to all forms of diabetes, such as type I and type II diabetes, as well as hyperinsulinemia and hyperlipidemia, e.g., obese subjects, and insulin-resistant diabetes, such as Mendenhall's Syndrome, Werner Syndrome, leprechaunism, lipoatrophic diabetes, and other lipoatrophies. The preferred hyperglycemic disorder is diabetes, especially type I and type II diabetes. "Diabetes" itself refers to a progressive disease of carbohydrate metabolism involving inadequate production or utilization of insulin and is characterized by hyperglycemia and glycosuria.

As used herein, the term "treating" refers to both therapeutic treatment and prophylactic or preventative measures. Those in need of treatment include those already with the disorder as well as those prone to having the disorder or diagnosed with the disorder or those in which the disorder is to be prevented. Consecutive treatment or administration refers to treatment on at least a daily basis without interruption in treatment by one or more days. Intermittent treatment or administration, or treatment or administration in an intermittent fashion, refers to treatment that is not consecutive, but rather cyclic in nature. The treatment regime herein can be either consecutive or intermittent, but preferably is consecutive when both proteins are formulated and administered together.

As used herein, "mammal" for purposes of treatment refers to any animal classified as a mammal, including humans, domestic, and farm animals, and zoo, sports, or pet animals, such as dogs, horses, cats, sheep, pigs, cows, etc. The preferred mammal herein is a human. The term "non-adult" refers to mammals that are from perinatal age (such as low-birth-weight infants) up to the age of puberty, the latter being those that have not yet reached full growth potential.

As used herein, the term "hypoglycemic agent" refers to secretagogues, preferably oral agents, excluding insulin, which cause the secretion of insulin by the pancreas. More preferred herein for human use are the sulfonylurea class of oral hypoglycemic agents. Examples include glyburide, glipizide, and gliclazide. In addition, agents that enhance insulin sensitivity, such as biguanides, are within this definition, and also are preferred.

As used herein, "complexed" in the context of polypeptides means that they are covalently bonded or otherwise have a binding affinity that is greater than about $1\ (m\mu)^{-1}$. Examples would include a complex of IGF-I and one or more of its binding proteins, or of a ligand and its receptor, or of methemoglobin and the tryptic fragment of bovine liver cytochrome b, or complex coacervation, as with albumin and acacia.

As used herein, "soluble" refers to polypeptides that, when in aqueous solutions, are completely dissolved, resulting in a clear to slightly opalescent solution with no visible particulates, as assessed by visual inspection. A further assay of the turbidity of the solution may be made by measuring UV absorbances at 320 to 360 nm with a 1-cm pathlength cell (Eckhardt et al., *J. Pharmaceutical Science and Technology*, 48: 64–70 (1994)).

A "stabilizer" is any compound that functions to preserve the active polypeptides in the formulation, e.g., insulin and IGF-I, so that they do not degrade or otherwise become inactive over a reasonable period of time or develop pathogens or toxins that prevent their use. Examples of stabilizers include preservatives that prevent bacteria, viruses, and fungi from proliferating in the formulation, anti-oxidants, or other compounds that function in various ways to preserve the stability of the formulation.

A "buffer" as used herein is any suitable buffer that is GRAS and generally confers a pH from about 4.8 to 8, preferably from about 7 to 7.5, most preferably about 7.2, if the polypeptides are IGF-I and insulin. Examples include acetic acid salt buffer, which is any salt of acetic acid, including sodium acetate and potassium acetate, succinate buffer, phosphate buffer, citrate buffer, histidine buffer, or any others known to the art to have the desired effect. The most preferred buffer is histidine for a pH of about 7 to 7.5.

B. Modes for Carrying out the Invention

Generally, the formulations are prepared by mixing the polypeptides of opposite charge, each at the desired degree of purity, uniformly and intimately with one another and with one or more of the following excipients: arginine, lysine, glutamate, or sodium dodecyl sulfate, or with a combination of the two excipients beta-hydroxy cyclodextrin and arginine. Optionally, the composition may also contain, for parenteral administration, a pharmaceutically or parenterally acceptable carrier, i.e., one that is non-toxic to recipients at the dosages and concentrations employed and is compatible with other ingredients of the formulation. For example, the formulation preferably does not include oxidizing agents and other compounds that are known to be deleterious to polypeptides. Preferably the carrier is a parenteral carrier, more preferably a solution that is isotonic with the blood of the recipient. Examples of such carrier vehicles include water, saline, or a buffered solution such as phosphate-buffered saline (PBS), Ringer's solution, and dextrose solution. Most preferably, the carrier vehicle is PBS.

The preferred excipients depend on the types of polypeptides being employed, the molar ratio of the two polypeptides in the composition, the presence, types, and amounts of other ingredients, etc. For example, if the polypeptides are IGF-I and insulin, the preferred excipient is arginine in a concentration of 100–200 mM, more preferably about 160 mM for a 1:1 vol/vol ratio of IGF-I and insulin. Further, if the insulin is NPH-insulin, it cannot have the beta-cyclodextrin sulfobutyl ether as excipient, alone or in combination with arginine, because it causes re-solubilization of insulin in the NPH portion, thereby dissociating NPH-insulin complex.

The composition preferably also contains a buffer that brings the pH to about 7–7.5, such as histidine, if the polypeptides are insulin and IGF-I.

The concentration of excipient employed also depends on the type and the ratio of the polypeptides. For example, if the excipient is arginine and the polypeptides are Regular insulin and IGF-I at an insulin concentration of 3.8 mg/ml and an IGF-I concentration of 10 mg/ml, the maximum ratio of insulin to IGF-I is 0.85:1 if the concentration of arginine is 150 mM. However, as the concentration of arginine is increased, the ratio of Regular insulin to IGF-I is increased, such that at 230 mM arginine, the maximum ratio is 2.5:1. When lysine or glutamate is employed as excipient at 280 mM, the maximum ratio is 1:1. Furthermore, the mixing ratio can be 1:1 to 6:1 When 0.5% SDS is employed. Mixing can be done at less than a 1.4:1 ratio when 5% beta-hydroxy cyclodextrin and 150 mM arginine are employed, less than 6:1 when 5% beta-hydroxy cyclodextrin and 230 mM arginine are employed, less than 0.25:1 if 1% beta-cyclodextrin sulfobutyl ether is used, less than 1.2:1 if 1% beta-cyclodextrin sulfobutyl ether and 150 mM arginine are used, and less than 10:1 if 5% beta-cyclodextrin sulfobutyl ether and 230 mM arginine, or 2.5% of such ether with 230 mM arginine, or 2% of such ether with 150 mM arginine are used.

The volume:volume ratio of the polypeptides depends mainly on the types of polypeptides, concentration of polypeptides, type(s) of excipient(s), and concentration(s) of excipient(s). For NPH-insulin, the ratio of insulin:IGF-I generally ranges from about 1:15 to 15:1 vol./vol., preferably about 11: to 15:1. For Regular insulin, the ratio generally varies from about 1:6 to 6:1, preferably from about 1:1 to 1:6. For 70/30 insulin, the pref range is from about 1:1 to about 6:1.

The polypeptides are typically formulated in such vehicles at a pH of from about 4.5 to 8, depending mainly on the pI of the polypeptides, preferably in the presence of a buffer that maintains the pH level. If the polypeptides are IGF-I and insulin, preferably the IGF-I is formulated at about pH 7 to 7.5, more preferably about 7.2, using histidine as buffer, before mixing with the insulin. The final preparation is a stable liquid.

In one embodiment for treating diabetes, the composition comprises IGF-I and NPH-insulin in a volume ratio of insulin:IGF-I of from about 15:1 to 1:15 (v/v). The more preferred amounts of IGF-I and insulin in this composition are from about 1 to 10 mg IGF-I and from about 0.2 to 2 mg insulin. The preferred volume:volume ratio of insulin:IGF-I is from about 0.2:1 to about 1:1.

The composition herein also may contain a stabilizer. For example, quaternary ammonium salts are useful stabilizers in which the molecular structure includes a central nitrogen atom joined to four organic (usually alkyl or aryl) groups and a negatively-charged acid radical. These salts are useful as surface-active germicides for many pathogenic non-sporulating bacteria and fungi and as stabilizers. Examples include octadecyldimethylbenzyl ammonium chloride, hexamethonium chloride, benzalkonium chloride (a mixture of alkylbenzyldimethylammonium chlorides in which the alkyl groups are long-chain compounds), and benzethonium chloride. Other types of stabilizers include aromatic alcohols such as phenol and benzyl alcohol, alkyl parabens such as methyl or propyl paraben, and m-cresol. The preferred stabilizer herein is phenol or benzyl alcohol, and the most preferred is phenol.

The stabilizer is included in a stable liquid form of the insulin and IGF-I formulation, but not in a lyophilized form of the formulation. In the latter case, the stabilizer is present in the bacteriostatic water for injection (BWFI) used for reconstitution.

One preferred composition containing IGF-I and an insulin contains at least arginine as well as a buffer that brings the pH to about 7 to 7.5, most preferably histidine, and a phenol, optionally with PBS. More preferably, the arginine is present in a concentration of about 100 to 300 mM and the ratio of insulin:IGF-I is from about 0.1:1 to 10:1, more preferably about 0.2:1 to about 1:1. In another preferred embodiment, this formulation with 100 to 300 mM arginine, as well as a buffer such as histidine and a phenol, also contains beta-cyclodextrin sulfobutyl ether as an excipient in a concentration of about 1–10%. A more preferred composition of this type comprises about 5–20 mg/ml IGF-I, about 2–10 mg/ml insulin, about 100–200 mM arginine, about 5–20 mM histidine at pH about 7–7.5, and about 1–5 mg/ml phenol. The most preferred composition comprises about 10 mg/ml IGF-I, about 3–4 mg/ml insulin, about 160 mM arginine, about 10 mM histidine, and about 3 mg/ml phenol, at pH about 7.2.

Another preferred composition containing IGF-I and an insulin contains sodium dodecyl sulfate as excipient in a concentration of about 1–10% and has a ratio of insulin:IGF-I of about 1:1 to 6:1.

The final formulation, if a liquid, is preferably stored at a temperature of from about 2 to 8° C. for a suitable time period. Alternatively, the formulation can be lyophilized and provided as a powder for reconstitution with water for injection that is stored as described for the liquid formulation.

The polypeptides to be used for therapeutic administration must be sterile. Sterility is readily accomplished by filtration through sterile filtration membranes (e.g., 0.2 micron membranes). Therapeutic compositions generally are placed into a container having a sterile access port, for example, an intravenous solution bag or vial having a stopper pierceable by a hypodermic injection needle.

The polypeptide composition ordinarily will be stored in unit or multi-dose containers, for example, sealed ampules or vials, as an aqueous solution or as a lyophilized formulation for reconstitution. As an example of a lyophilized formulation, 10-mL vials are filled with 5 mL of sterile-filtered 1% (w/v) aqueous IGF-I solution, and the resulting mixture is lyophilized. The subcutaneous injection solution is prepared by reconstituting the lyophilized insulin using bacteriostatic Water-for-Injection. This solution is then mixed with a similarly reconstituted insulin solution or a liquid insulin solution.

The formulation containing both the IGF-I and insulin can be made by many different methods. One method comprises mixing insulin with an IGF-I-containing composition (having the ingredients as described below).

The IGF-I-containing solution useful for administering with the insulin solution as described above preferably contains arginine, more preferably contains arginine and a stabilizer, still more preferably contains arginine, a stabilizer, and a buffer, and more preferably is as follows: About 5–20 mg/ml IGF-I, about 100–200 mM arginine, about 5–20 mM buffer at about pH 7–7.5, and about 1–5 mg/ml phenol. The most preferred compositio for this purpose comprises about 10 mg/ml IGF-I, about 160 mM arginine, about 10 mM histidine at about pH 7.2, and about 3 mg/ml phenol.

Kits are also contemplated for this invention. A typical kit would comprise a container, preferably a vial, for a first polypeptide such as IGF-I in an excipient as described above; a container, preferably a vial, comprising a second polypeptide of the opposite charge; and instructions, such as a product insert or label, directing the user to combine the contents of the two containers, i.e., the two formulations. This would preferably provide a pharmaceutical formulation. Preferably, if the polypeptides are IGF-I and insulin, the pharmaceutical formulation is for treating diabetes. Also, preferably the container with IGF-I additionally comprises a stabilizer such as benzyl alcohol or phenol, or both, in the buffer at a pH of from about 7.0 to 7.5. Preferably, the user will be instructed to combine the contents of the containers, i.e., the two formulations, in a syringe for immediate injection.

Another typical kit is one where the composition is already prepared such that it is contained in one container and the kit also has instructions for using the composition to treat an appropriate disorder.

The composition of polypeptides is directly administered to the mammal by any suitable technique, including infusion, injection, and pulmonary and transdermal administration. The specific route of administration will depend, e.g., on the medical history of the patient, including any perceived or anticipated side effects using either polypeptide alone, the types of polypeptides employed, and the particular disorder to be corrected. Examples of parenteral administration include subcutaneous, intramuscular, intravenous, intraarterial, and intraperitoneal administration of the composition.

One preferred method of delivery for systemic-acting drugs involves administration by continuous infusion (using, e.g., slow-release devices or minipumps such as osmotic pumps or skin patches), or by injection (using, e.g., intravenous or subcutaneous means, including single-bolus administration). For example, if the polypeptides are insulin and IGF-I, delivery of the composition by injection will be the preferred form of administration for treating diabetes.

Another preferred route of administration is iontophoretic transdermal delivery either for localized or systemic therapy. Iontophoresis is a means of in enhancing the flux of ionic drugs across skin by the application of an electrochemical potential gradient. Drugs suitable for this method of delivery include LHRH analogues, insulin, growth hormone, and cholecystokinin-8 analogues. See, for example, Srinivasan et al., *J. Pharm. Sci.*, 79: 588–591 (1990).

The composition to be used in the therapy will be formulated and dosed in a fashion consistent with good medical practice, taking into account the clinical condition of the individual patient (especially the side effects of treatment with the polypeptides as single agents), the site of delivery of the composition, the types of polypeptides employed, the method of administration, the scheduling of administration, and other factors known to practitioners. The "effective amounts" of each component for purposes herein are thus determined by such considerations and must be amounts that result in bioavailability of the drugs to the mammal.

As a general proposition, the total pharmaceutically effective amount of the polypeptides administered parenterally per dose will be in the range of from about 10 $\mu$g/kg/day to about 1 mglkg/day based on kg of patient body weight. For the combination of IGF-I and insulin, the parenteral amount per dose ranges from about 10 to 200 $\mu$g/kg/day of IGF-I based on kg of patient body weight, and from about 0.5 to 500 units/day of insulin, although, as noted above, this will be subject to a great deal of therapeutic discretion. Preferably for treatment of diabetes in humans, the dose of IGF-I is from about 1 to 10 mg twice per day, more preferably from about 20 to 80 $\mu$g/kg/injection (i.e., from about 1.5 to 6 mg) twice a day subcutaneously, and the dose of insulin is from about 5 to 50 units/injection (i.e., from about 0.2 to 2 mg) twice a day subcutaneously. The ratio of insulin to IGF-I in this formulation by volume is that referred to above.

Although injection is preferred, an infusion device may also be employed for continuous subcutaneous (SC) infusions. An intravenous bag solution may also be employed. The key factor in selecting an appropriate dose is the result obtained, for example, in the case of diabetes as measured by decreases in blood glucose so as to approximate the normal range, or by other criteria for measuring treatment of diabetes as defined herein as are deemed appropriate by the practitioner. Further information on dosing insulin can be found in *Diabetes Mellitus—Theory and Practice*, supra, Chapters 29 and 30.

Also, the formulation herein is suitably administered along with other agents that produce the desired pharmacological effect, for example, in the case of IGF-I and insulin, an IGF binding protein, for example, one of those currently known, i.e., IGFBP-1, IGFBP-2, IGFBP-3, IGFBP-4, IGFBP-5, or IGFBP-6, or with the ALS of the IGF binding complex. The preferred binding protein for IGF-I herein is IGFBP-3, which is described in U.S. Pat. No. 5,258,287 and by Martin and Baxter, *J. Biol. Chem.*, 261: 8754–8760 (1986). This glycosylated IGFBP-3 protein is an acid-stable component of about 53 Kd on a non-reducing SDS-PAGE gel of a 125–150 Kd glycoprotein complex found in human plasma that carries most of the endogenous IGFs and is also regulated by GH.

The administration of the IGF binding protein with IGF-I and insulin may be accomplished by the method described in U.S. Pat. No. 5,187,151. Briefly, the IGF-I and IGFBP are administered in effective amounts by subcutaneous bolus injection in a molar ratio of from about 0.5:1 to 3:1, preferably about 1:1; the insulin is already present with the IGF-I.

Furthermore, the formulation is suitably administered along with an effective amount of a hypoglycemic agent such as a sulfonylurea. The hypoglycemic agent is administered to the mammal by any suitable technique including parenterally, intranasally, orally, or by any other effective route. Most preferably, the administration is by the oral route. For example, MICRONASE® (glyburide tablets, USP) marketed by Pharmacia & Upjohn Company in 1.25-, 2.5-, and 5-mg tablet concentrations are suitable for oral administration. The usual maintenance dose for Type II diabetics, placed on this therapy, is generally in the range of from about 1.25 to 20 mg per day, which may be given as a single dose or divided throughout the day as deemed appropriate (*Physician's Desk Reference*, 2563–2565 (1995)). Other examples of glyburide-based tablets available for prescription include GLYNASE® micronized glyburide (Pharmacia & Upjohn Company) and DIAβETA® glyburide, USP (Hoechst-Roussel Pharmaceuticals). GLUCOTROL® (Roerig) glipizide (1-cyclohexyl-3-(p-(2-(5-methylpyrazine carboxamide)ethyl)phenyl)sulfonylurea) comes in tablets available in both 5- and 10-mg strengths and is also prescribed to Type II diabetics who require hypoglycemic therapy following dietary control or in patients who have ceased to respond to other sulfonylureas (*Physician's Desk Reference*, 1902–1903 (1995)). Other hypoglycemic agents than sulfonylureas, such as the biguanides (e.g., metformin and phenformin) or troglitozones, or other drugs affecting insulin action may also be employed.

The invention will be more fully understood by reference to the following examples. They should not, however, be construed as limiting the scope of the invention. All literature and patent citations mentioned herein are expressly incorporated by reference.

EXAMPLE I

Materials and Methods

Recombinant human IGF-I was obtained from Genentech, Inc. HUMULIN® R (regular insulin human injection, USP (rDNA origin)) and HUMULIN® 70/30 (70% human insulin isophane suspension, 30% human insulin injection (DNA origin)) were obtained from Eli Lilly and Company. The 0.5-cc and 1-cc insulin syringes were obtained from Becton Dickinson, and PD-10® desalting columns (SEPHADEX™ G25M crosslinked dextran ion exchanger) were obtained from Pharmacia Biotechnology AB (catalog #17-0851-01).

Table 1 lists formulation dosage forms for Regular, NPH-, and 70/30 insulin.

| | |
|---|---|
| HUMULIN ® R (regular insulin human injection, USP (rDNA origin)) | zinc-insulin, 100 USP units, 3.8 mg/ml<br>10 μg–40 μg zinc/100 USP units<br>2.5 mg/ml m-cresol<br>16 mg/ml glycerine<br>pH-7.2 |
| HUMULIN ® N (NPH human insulin (rDNA origin) isophane suspension) | 100 USP units/ml, 3.8 mg/ml<br>3–6 mg protamine<br>16 mg/ml glycerine<br>1.6 mg/ml m-cresol<br>10–40 μg zinc/100 USP<br>0.65 mg/ml phenol<br>phosphate, pH-7.2 |
| HUMULIN ® 70/30 (70% human insulin isophane suspension, 30% human insulin injection (DNA origin)) | 100 USP units/ml, 3.8 mg/ml<br>approximately 2.5 mg protamine<br>phosphate, pH-7.2<br>m-cresol<br>zinc<br>phenol |

Preparation of IGF-I for Formulation Screen

IGF-I in 0.2 M citrate, 26 mg/ml, was used as the starting material. Citrate was difficult to remove from IGF-I solutions. Therefore, a two-step diafiltration process was designed to remove citrate and at the same time increase IGF-I concentration. Diafiltration was accomplished using a tangential flow filtration unit. The process steps were as follow:

(a) The IGF-I solution containing 200 mM citrate was first diafiltered into 200 mM NaCl, 230 mM arginine, and 10 mM histidine at pH 7.2.

(b) The IGF-I solution was then diafiltered into 230 mM arginine, 10 mM histidine, pH 7.2 IGF-I was concentrated to 28.6 mg/ml.

Arginine was used in both steps due to its ability to keep IGF-I in solution at high concentrations at pH 7.2. Thus, removing citrate and concentrating IGF-I could be accomplished without precipitating IGF-I. The above IGF-I solution was then buffer-exchanged into various testing formulations using PD-10® desalting columns.

Assay Methods (1) Visual inspection: color, appearance and clarity;
(2) pH;
(3) IGF-I concentration: determined by UV absorbance at 276 nm using an absorptivity of 0.646 $cm^{-1}$ $(mg/ml)^{-1}$;
(4) solution turbidity: determined by UV absorbance at 340 to 360 nm;
(5) quantitation of IGF-I and insulin in solution: detrmined by the acidic pH reversed-phase HPLC (rp-HPLC) method:

| | | |
|---|---|---|
| Column: | VYDAC ® reversed-phase HPLC (Grace Vydac) C18, 300Å, 25 cm | |
| Flow rate: | 0.5 ml/minute | |
| Injection volume: | 25 μl/injection | |
| Detection wavelength: | 214 nm | |
| Column temperature: | 50□C | |
| Solvent A: | 0.1% trifluroacetic acid in $H_2O$ | |
| Solvent B: | 0.1% trifluroacetic acid in acetonitrile | |
| Gradient: | time | % A |
| | 0 | 72 |
| | 20 | 72 |
| | 25 | 70.5 |
| | 40 | 61.5 |
| | 50 | 40 |
| | 51 | 72 |
| | 60 | 72 |

Figure 2:
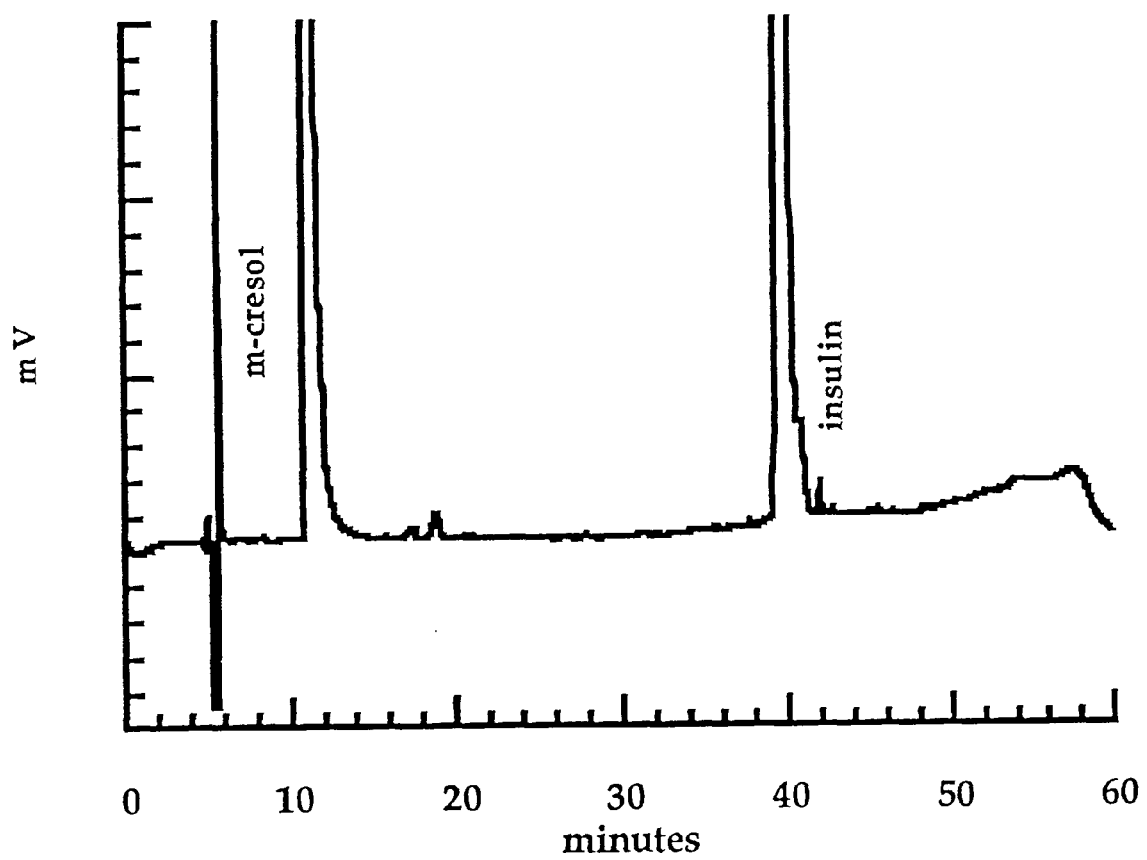
FIG. 2 shows the acidic pH reversed-phase HPLC chromatogram of Regular insulin.
Figure 3:
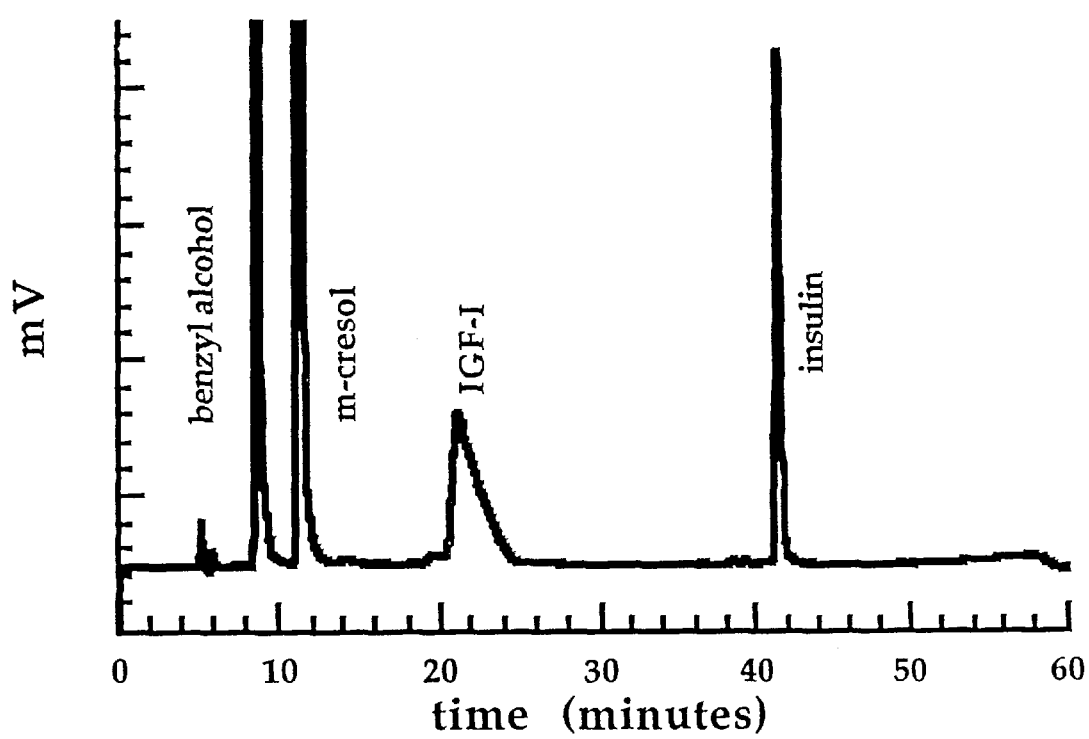
FIG. 3 shows the acidic pH reversed-phase HPLC chromatogram for an IGF-I and insulin mixture.

FIG. 1 shows the acidic reversed-phase HPLC of an IGF-I sample. FIG. 2 shows the acidic reversed-phase HPLC of Regular insulin. FIG. 3 shows the acidic reversed-phase HPLC of a 1:1 (vol.:vol.) mixture of Regular insulin: IGF-I.

It is evident from comparing and reviewing these Figures that IGF-I and Regular insulin are well separated by this HPLC method. Quantitation of both IGF-I and insulin can be achieved by utilizing the peak areas of IGF-I and insulin peaks. For example, the percentage of IGF-I remaining in solution can be obtained by comparing the IGF-I peak areas before and after IGF-I is mixed with insulin.

Procedure for Mixing IGF-I and Insulin (1) Draw air into an insulin syringe equal to dosage of IGF-I. Insert needle into IGF-I vial, and inject air into bottle. Remove needle/syringe from the IGF-I vial without withdrawing any IGF-I solution.

(2) For NPH and 70:30 insulin, gently invert insulin vial several times before use. No mixing is required for Regular insulin. Inject air into the insulin vial.

(3) With the needle still in the insulin vial, turn insulin bottle and syringe upside down.

(4) Make sure the tip of the needle is in solution, and withdraw correct volume of insulin into syringe.

(5) Before removing needle from the insulin vial, check the syringe for air bubbles. If air bubbles are present, hold syringe straight up and tap its side, until bubbles float to the top. Push them out with plunger and withdraw correct insulin dose.

(6) Remove needle from the insulin vial and insert it into the IGF-I vial. Turn IGF-I bottle and syringe upside down. Make sure the tip of the needle is in the solution, and withdraw desired amount of IGF-I into syringe.

(7) Remove needle/syringe from the IGF-I vial, and inject insulin/IGF-I mixture into a clean glass centrifuge tube.

Analysis Procedures for the Insulin/IGF-I Mixture

The IGF-I/insulin mixture was assayed for soluble IGF-I and insulin content either after filtration through a 0.2 μm filter or after centrifugation at 2000 r.p.m. for 10 minutes. In some cases, the IGF-I and insulin mixture was first incubated with phosphate-buffered saline at 37° C. for 10 minutes before the mixture was filtered or centrifuged for analysis.

Results and Discussion

Mixability of the Acetate-buffered IGF-I Formulation With Insulin:

The acetate-buffered IGF-I formulation used as a standard herein is a clear liquid and contains 10 mg/ml IGF-I, 100 mM sodium chloride, 2 mg/ml polysorbate 20, 9 mg/ml benzyl alcohol, 50 mM acetate, pH 5.4. This product is intended for multi-use purposes for up to 28 days of use. Shelf life was set at 60 months at 2–8° C. storage. The mixability of the acetate-buffered IGF-I formulation with insulin was first evaluated. It would be most desirable if this IGF-I formulation could be used to mix with insulin during administration.

Table 2 shows results of mixing the acetate-buffered IGF-I formulation with Regular insulin. At 1:1 (vol:vol) mixing ratio, the solution turned very cloudy upon mixing. 43% of insulin and 14% of IGF-I precipitated out of solution.

TABLE 2

IGF-I in the acetate formulation mixed with Regular insulin

| Mixing Ratio (Regular insulin: IGF-I) (vol:vol) | % IGF-I in Solution | % Insulin in Solution |
|---|---|---|
| 1:1 | 86% | 57% |

Figure 4:
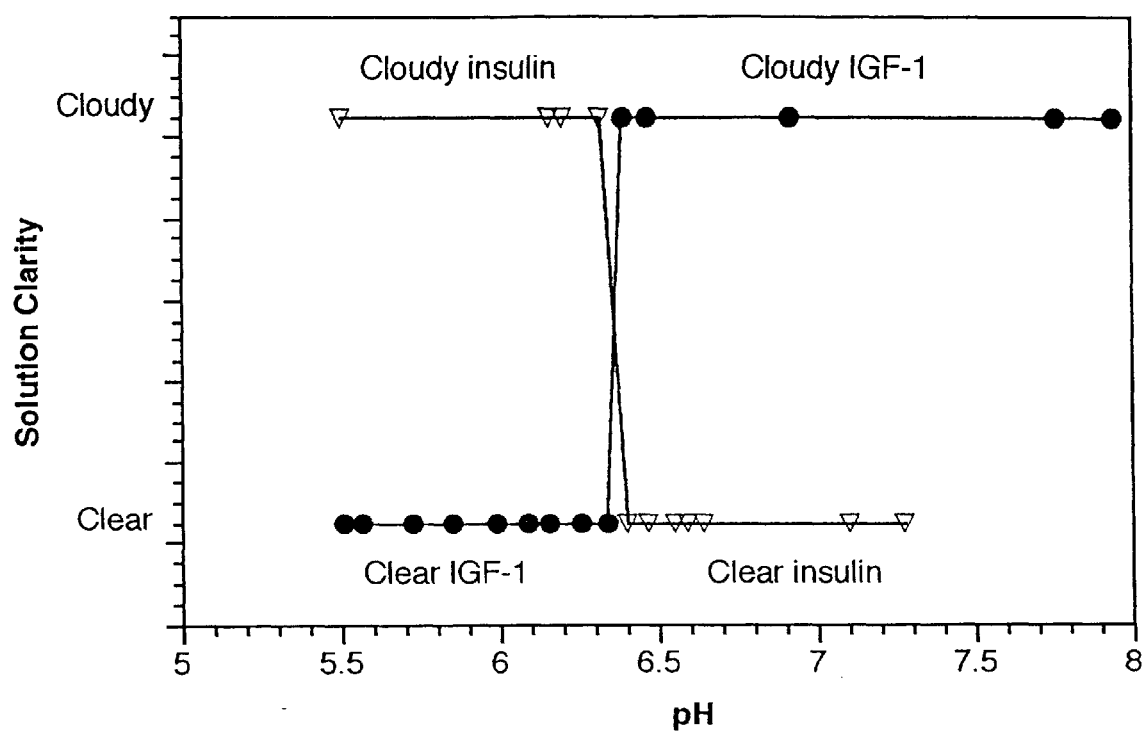
FIG. 4 shows a graph of solution clarity of Regular insulin (triangles) or IGF-I in an acetate-buffered formulation used as a control herein (circles) as a function of solution pH, which was adjusted by adding 0.1N HCl or NaOH.

The appearance of Regular insulin and IGF-I in the acetate formulation was monitored as the pH of these solutions was adjusted by adding 0.1N HCl or NaOH. The solution was characterized as either "clear" or "turbid", and solution clarity vs. pH is plotted in FIG. 4. Regular insulin at pH 7.2 is a clear solution, and it remains clear above pH 6.4; the Regular insulin solution turns cloudy at pH 6.32 or below. IGF-I in the acetate formulation at pH 5.4 is a clear solution and remains clear below pH 6.34. IGF-I solution turns cloudy above pH 6.39, and the precipitated IGF-I subsequently turns into a clear gel. These observations are consistent with the general understanding that protein solubility decreases as pH approaches the protein's isoelectric point (pI). The isoelectric points of IGF-I and insulin are 8.7 and 5.4, respectively. Data shown in FIG. 4 suggest that no suitable pH range exists at which both IGF-I and Regular insulin can stay in solution. Therefore, it is not possible simply to adjust the pH of the acetate IGF-I formulation to produce a clear IGF-I/insulin mixture.

Table 3 shows the result of mixing the acetate IGF-I formulation with NPH-insulin at various mixing ratios. At NPH-insulin:IGF-I mixing ratios of 1:1 and 14:1 (vol:vol), both NPH-insulin and IGF-I were unchanged before and after mixing. All IGF-I remained in solution and all NPH-insulin remained as NPH crystals with no soluble insulin in solution. However, when NPH-insulin and IGF-I were mixed at a 1:14 (vol:vol) ratio, 100% of the insulin was released from the NPH crystals, although IGF-I remained unchanged.

TABLE 3

IGF-I in the acetate formulation mixed with NPR-insulin

| Mixing Ratio (NPR-insulin:IGF-I) (vol:vol) | % IGF-I in Solution | % Insulin in Solution |
|---|---|---|
| 14:1 | 93% | 0.64% |
| 1:1 | 93% | 0.8% |
| 1:14 | 93% | 100% |

Development of New IGF-I Formulation Mixable With Insulin:

Due to the inability of the acetate IGF-I formulation to mix with insulin, a new formulation was developed that meets the following criteria: (1) A clear IGF-I solution formulated at pH 7.2. This serves to prevent drastic pH shifts when IGF-I and insulin are mixed at wide ranges of mixing ratios. (2) An IGF-I formulation that prevents insulin and IGF-I interaction upon mixing, so as to avoid precipitation of insulin and/or IGF-I. (3) An IGF-I formulation that will not dissociate insulin from NPH crystals upon mixing. During the development of such an IGF-I formulation, various excipients such as salts, buffers, metal ions, sugars, amino acids, polyols, surfactants, and cyclodextrins were screened as listed in Table 4.

TABLE 4

Excipients Screened for the Development of a New IGF-I Formulation for Mixing with Insulin

| Excipient | Excipient Concentration |
|---|---|
| Sodium Chloride | 200 mM |
| Sodium Sulfate | 200 mM |
| Sodium Phosphate | 250 mM |
| Sodium Citrate | 125–500 mM |
| Sodium Bicarbonate | 250 mM |
| Sodium Ascorbate | 250–500 mM |
| Sodium Succinate | 125–250 mM |
| Sodium Alginate | 1% |
| Heparin Sulfate | 0.25% |
| Calcium Chloride | 50–300 mM |
| Magnesium Chloride | 50–300 mM |
| EDTA | 40 mM |
| Glycerol | 200 mM |
| Sucrose | 300 mM |
| Trehalose | 300 mM |
| Mannitol | 300 mM |
| Glycine | 140 mM–280 mM |
| Lysine | 140 mM–280 mM |
| Histidine | 140 mM–280 mM |
| Glutamate | 140 mM–280 mM |
| Arginine | 140 mM–280 mM |
| Aspartate | 140 mM |
| Guanidine Hydrochloride | 140 mM |
| TWEEN ® 20 polyoxyethylene sorbitan monolaurate (Atlas Chemical Co.) | 0.5%–2% |
| TWEEN ® 80 polyoxyethylene sorbitan monooleate (Atlas Chemical Co.) | 0.5% |
| Triton X-100 ™ octylphenol ethylene oxide condensate; non-ionic detergent (Sigma-Aldrich, Inc./Union Carbide) | 0.5% |
| PLURONIC ® F-68-LF block copolymer surfactant of propylene oxide and ethylene oxide (BASF Corp.) | 0.5% |
| Sodium Dodecyl Sulfate (SDS) | 0.05%–0.5% |
| PEG 6000 | 5% |
| β-Hydroxy cyclodextrin | 1%–17% |
| β-Cyclodextrin Sulfobutyl Ether | 1%–30% |

The control acetate-buffered IGF-I formulation turned cloudy when the pH was adjusted to above 6.4. Many of the excipients listed in Table 4 enabled IGF-I to be a clear solution at pH 7.2. These excipients included amino acids (glycine, lysine, arginine, histidine, glutamate, aspartate), salts (sodium chloride, sulfate, phosphate, citrate, bicarbonate, ascorbate, succinate), cyclodextrin derivatives (β-hydroxy cyclodextrin and β-cyclodextrin sulfobutyl ether), SDS, and glycerol. However, upon mixing of IGF-I and Regular insulin, most of the excipients above were not able to prevent insulin and IGF-I precipitation.

The excipients that proved to be effective in preventing precipitation of Regular insulin and IGF-I upon mixing were arginine, lysine, glutamate, SDS, β-hydroxy cyclodextrin and β-cyclodextrin sulfobutyl ether. Mixing results using these excipients are shown in Table 5. 0.5% SDS was very effective in achieving a clear insulin and IGF-I mixture. However, when 0.5% SDS was added to NPH-insulin at a 1:1 (vol:vol) ratio, the solution clarified, which indicated the dissolution of NPH crystals. Both lysine and glutamate when used at a concentration of 280 mM prevented precipitation upon 1:1 (vol:vol) mixing of IGF-I and Regular insulin.

TABLE 5

Excipient Effects on the Appearance of IGF-I/Regular Insulin Mixture (a)

| Excipient | Excipient Concentration | Mixing Ratio R-insulin:IGF-I (vol:vol) | Mixture Appearance |
|---|---|---|---|
| No Excipient | — | any ratio | Cloudy |
| SDS | 0.5% | 1:1 | Clear |
| | | 6:1 | Clear |
| Lysine | 140 mM | 1:1 | Cloudy |
| | 230 mM | 1:1 | Cloudy |
| | 280 mM | 1:1 | Clear |
| Glutamate | 150 mM | 1:1 | Cloudy |
| | 280 mM | 1:1 | Clear |
| Arginine | 150 mM | <0.85:1 (b) | Clear |
| | | ≧0.85:1 (b) | Cloudy |
| | 180 mM | 1:1 | Cloudy |
| | 230 mM | <2.5:1 (c) | Clear |
| | | ≧2.5:1 (c) | Cloudy |
| | 280 mM | 1:1 | Clear |
| beta-Hydroxy Cyclodextrin | 5% | any ratio | Cloudy |
| beta-Hydroxy Cyclodextrin and Arginine | 5% and 150 mM | <1.4:1 (c) | Clear |
| | | ≧1.4:1 (c) | Cloudy |
| | 5% and 230 mM | <6:1 (c) | Clear |
| | | ≧6:1 (c) | Cloudy |
| beta-Cyclodextrin Sulfobutyl Ether | 1% | <0.25:1 (c) | Clear |
| | | ≧0.25:1 (c) | Cloudy |
| beta-Cyclodextrin Sulfobutyl Ether and Arginine | 1% and 150 mM | <1.2:1 (c) | Clear |
| | | ≧1.2:1 (c) | Cloudy |
| | 5% and 230 mM | ≦10:1 (d) | Clear |
| | 2.5% and 230 mM | ≦10:1 (d) | Clear |
| | 2% and 150 mM | ≦10:1 (d) | Clear |

(a) In addition to the excipients listed in the Table, all IGF-I formulations contain 10 mg/ml IGF-I and 10 mM histidine at pH 7.2.
(b) Regular insulin was slowly added to 200 ml of 10 mg/ml IGF-I in 150 mM arginine, 10 mM histidine at pH 7.2. The solution remained clear until 170 ml of Regular insulin was added. 170 ml:200 ml = 0.85:1 mixing ratio.
(c) Mixing was done similarly as described in (b).
(d) Under these conditions, Regular insulin was slowly added to 200 ml of IGF-I. The mixed solution remained clear even after 2 ml of Regular insulin was added.

Arginine was more effective than lysine or glutamate in keeping both insulin and IGF-I in solution. As shown in Table 5, at 150 mM arginine concentration, Regular insulin and IGF-I could be mixed at mixing ratios up to 0.85:1 (vol:vol). When mixing ratios exceeded 0.85:1, precipitation of both IGF-I and insulin occurs. At 230 mM arginine concentration, more Regular insulin could be mixed with IGF-I to form a clear mixture, up to a mixing ratio of 2.5:1 (vol:vol).

Without being limited to any one theory, the protection against precipitation offered by arginine is believed to be due to the fact that at pH 7.2 insulin molecules are negatively charged, and the positively-charged arginine molecules interact with negatively-charged insulin, thereby shielding the interaction and subsequent precipitation between positively-charged IGF-I and negatively-charged insulin. High concentrations of arginine are required for mixing at a high insulin:IGF-I ratio.

As shown in Table 5, 1% β-cyclodextrin sulfobutyl ether allows mixing of Regular insulin and IGF-I at a mixing ratio below 0.25:1. Use of 5% β-hydroxy cyclodextrin did not allow mixing at any ratio. Use of both cyclodextrin and arginine is extremely effective in preventing insulin and IGF-I precipitation upon mixing. β-cyclodextrin sulfobutyl ether used at a concentration of 2% to 5% together with arginine used at a concentration of 150 mM to 230 mM allowed Regular insulin and IGF-I to be mixed at a very wide range of mixing ratios, up to 10:1 (insulin vol:IGF-I vol). Without being limited to any one theory, it is believed that this is due to the fact that at pH 7.2, positively-charged arginine interacts with negatively-charged insulin, and negatively-charged β-cyclodextrin sulfobutyl ether interacts with positively-charged IGF-I, thereby preventing insulin and IGF-I interaction and subsequent precipitation. However, in the presence of β-cyclodextrin sulfobutyl ether, NPH-insulin crystals dissolved. Without limitation to any one theory, this is presumably due to the strong interaction of β-cyclodextrin sulfobutyl ether with positively-charged protamine, which breaks the protamine-insulin complex. Therefore, although the use of both β-cyclodextrin sulfobutyl ether and/or SDS and arginine in the IGF-I formulation proves to be extremely effective in mixing with Regular insulin, it cannot be used to mix with NPH-insulin.

The above excipient screening study results identified arginine to be the preferred choice of excipient for an IGF-I formulation to be mixed with both Regular and NPH-insulin. A study was then carried out to evaluate the effect of arginine concentration on the ability of IGF-I to mix with insulin. The IGF-I formulation tested in this study contained 10 mg/ml IGF-I, 10 mM histidine, pH 7.2, 3 mg/ml phenol, and varying amounts of arginine. Insulin and IGF-I were mixed at various mixing ratios. Percent soluble IGF-I and insulin were assayed by the acidic reversed-phase HPLC method. Results in Table 6 showed that for mixing with Regular insulin, a high concentration of arginine is required. At 80 mM of arginine concentration, 39% of IGF-I and 68% of insulin precipitated when mixed at a 1:1 (vol:vol) ratio. At 230 mM of arginine concentration, all insulin and all IGF-I remained in solution when mixed at a 1:1 ratio. However, at 230 mM arginine concentration, when mixed at a 5:1 (vol:vol) IGF-I:NPH-insulin ratio, nearly 50% of NPH dissolved into soluble insulin. 160 mM arginine seemed to produce the best results for mixing with both Regular and NPH-insulin. At a 1:1 (R-insulin:IGF-I) mixing ratio, essentially all of Regular insulin and IGF-I remained in solution. At a 1:1 (NPH-insulin:IGF-I) mixing ratio, nearly 100% of NPH-insulin was in solution and all NPH crystals remained intact.

A preferred IGF-I formulation for mixing with insulin was therefore defined to be 10 mg/ml IGF-I, 160 mM arginine, 10 mM histidine at pH 7.2 and 3 mg/ml phenol. The mixability of this formulation with Regular, NPH-, and 70/30 insulin at various mixing ratios was assessed and results are tabulated in Tables 7, 8 and 9, respectively.

TABLE 7

Mixing Results for the New IGF-I Formulation Mixed with Regular Insulin (a)

| Mixing Ratio (Regular insulin: IGF-I) (vol:vol) | % IGF-I in Solution (b) (c) | % Insulin in Solution (b) (c) |
| --- | --- | --- |
| 1:6 | 96% | 100% |
| 1:1 | 95% | 99% |
| 2:1 | 89% | 89% |
| 6:1 | 91% | 93% |

(a) The new IGF-I formulation contained 10 mg/ml IGF-I, 160 mM arginine, 10 mM histidine at pH 7.2 and 3 mg/ml phenol.
(b) To simulate subcutaneous depot condition, after mixing of IGF-I and Regular insulin, 1 ml of the mixture was first incubated with 2 ml of phosphate buffered saline at 37° C. for 15 min before the amount of soluble insulin and IGF-I were analyzed.
(c) If IGF-I and Regular insulin are fully mixable, the resulting mixture should have 100% soluble IGF-I and 100% soluble insulin.

TABLE 8

Mixing Results for the New IGF-I Formulation Mixed with NPH-insulin (a)

| Mixing Ratio (NPH-insulin:IGF-I) (vol:vol) | % IGF-I in Solution (b) | % Insulin in Solution (b) |
| --- | --- | --- |
| 1:15 | 100% | 24% |
| 1:5 | 102% | 11% |
| 1:1 | 103% | 0.5% |
| 15:1 | 100% | 0.5% |

(a) The new IGF-I formulation contains 10 mg/ml IGF-I, 160 mM arginine, 10 mM histidine at pH 7.2 and 3 mg/ml phenol.
(b) If IGF-I and NPH-insulin are fully mixable, the resulting mixture should have 100% soluble IGF-I and 0% soluble insulin.

TABLE 6

Effect of Arginine concentration on the mixability of IGF-I(a) with Regular and NPH-insulin

| | IGF-I mix with Regular insulin (b,c) | | | IGF-I mix with NPH-insulin (d) | | |
| --- | --- | --- | --- | --- | --- | --- |
| Arginine Concentration | Mixing ratio insulin:IGF-I (vol:vol) | % IGF-I in solution | % insulin in solution | Mixing ratio insulin:IGF-I (vol:vol) | % IGF-I in solution | % insulin in solution |
| 80 mM | 1:1 | 61% | 32% | — | — | — |
| 100 mM | 1:1 | 69% | 60% | — | — | — |
| 160 mM | 1:1 | 96% | 100% | 1:1 | 100% | 0.7% |
| 200 mM | — | — | — | 5:1 | 100% | 30% |
| 230 mM | 1:1 | 100% | 100% | 1:1 | 100% | 0% |
| 230 mM | 9:1 | 100% | 100% | 9:1 | 100% | 0% |
| 230 mM | — | — | — | 1:3 | 100% | 7% |
| 230 mM | — | — | — | 1:5 | 100% | 43% |

(a) The IGF-I formulation tested in this study contained 10 mg/ml IGF-I, 10 mM histidine, pH 7.2, 3 mg/ml phenol, and varying amounts of arginine.
(b) To simulate subcutaneous depot condition, after mixing of IGF-I and Regular insulin, 1 ml of the mixture was first incubated with 2 ml of phosphate-buffered saline at 37° C. for 15 min before the amounts of soluble insulin and IGF-I were analyzed.
(c) If IGF-I and Regular insulin are fully mixable, the resulting mixture should have 100% soluble IGF-I and 100% soluble insulin.
(d) If IGF-I and NPH-insulin are fully mixable, the resulting mixture should have 100% soluble IGF-I and 0% soluble insulin.

TABLE 9

Mixing Results for the New IGF-I Formulation Mixed with 70:30 Insulin (a)

| Mixing Ratio (70/30 insulin:IGF-I) (vol:vol) | % IGF-I in Solution (b) | % Insulin in Solution (b) |
|---|---|---|
| 1:15 | 100% | 58% |
| 1:6 | 100% | 44% |
| 1:1 | 100% | 26% |
| 2:1 | 100% | 21% |
| 6:1 | 100% | 22% |

(a) The new IGF-I formulation contained 10 mg/ml IGF-I, 160 mM arginine, 10 mM histidine at pH 7.2 and 3 mg/ml phenol.
(b) If IGF-I and 70:30 insulin are fully mixable, the resulting mixture should have 100% soluble IGF-I and 22% to 30% of soluble insulin. 70/30 insulin theoretically should contain 30% soluble insulin. However, due to adsorption of soluble insulin onto NPH-insulin, the actual amount of soluble insulin is 22% by the acidic reversed-phase HPLC method.

When the preferred IGF-I formulation was mixed with Regular insulin at a 1:1 (vol:vol) ratio, the solution turned turbid. 65% of IGF-I and 93% of insulin were in solution when assayed directly after mixing. However, after this mixture was incubated in phosphate-buffered saline at 37° C. for 15 minutes to simulate the subcutaneous depot condition, the solution clarified and 95% of IGF-I and 99% of insulin were in solution. Table 7 shows IGF-I and Regular insulin mixing results after the mixtures were incubated with phosphate-buffered saline at 370C for 15 minutes. When mixed at 1:1, 2:1, 6:1 (Regular insulin:IGF-I) ratios, precipitation occurred initially. However, the mix clarified upon incubation with phosphate-buffered saline and the percent soluble IGF-I and insulin was nearly 90% or above. Therefore, the pharmacokinetic profiles of IGF-I and insulin may not result in much change before and after mixing.

When the preferred IGF-I formulation was mixed with NPH-insulin at a mixing ratio from 1:15 to 15:1 (vol:vol) ratio, the solution remained cloudy, indicating the presence of intact NPH-insulin. As shown in Table 8, at mixing ratios between 1:1 to 15:1 (NPH-insulin:IGF-I), all IGF-I was in solution and all NPH remained as insulin-protamine complex. At low NPH-insulin:IGF-I mixing ratios, a sufficient amount of arginine in the preferred formulation started to dissociate NPH. The amount of NPH dissociation was relatively low (24%) even at the extreme of 1:15 mixing ratio. Therefore, at most of the mixing ratios, the pharmacokinetic profiles of IGF-I and insulin may not result in much change before and after mixing.

Table 9 shows the result of mixing the preferred IGF-I formulation with 70/30 insulin. Theoretically, the 70/30 insulin should contain 30% soluble insulin. However, soluble insulin tended to adsorb onto the NPH-insulin crystals. The actual amount of soluble insulin in the 70/30 insulin was 22% by the acidic reversed-phase HPLC method. If IGF-I and 70/30 insulin were fully mixable, the resulting mixture should have 100% soluble IGF-I and 22% to 30% of soluble insulin. Results in Table 9 show that the percent soluble IGF-I and insulin did not change when 70/30 insulin and IGF-I were mixed at ratios of 1:1 to 6:1 (vol:vol). At low 70/30 insulin:IGF-I mixing ratios, a portion of the NPH dissolved into soluble insulin.

In all of the above studies, no chemical degradation of either IGF-I or insulin was observed as a result of mixing by the acidic reversed-phase HPLC assay.

CONCLUSIONS

To reduce the frequency of injections and improve patient compliance, it is desirable to mix polypeptides of opposite charges and then co-administer them. In this Example, the compatibility of IGF-I in the control acetate-buffered formulation and insulin was first evaluated. Immediately after mixing Regular insulin with IGF-I in the acetate formulation, the mixture turned from a clear solution into a cloudy suspension, indicating precipitation of both IGF-I and insulin. When mixed with NPH-insulin, the acetate-buffered IGF-I formulation dissociated NPH-insulin-protamine complex at low NPH/IGF-I mixing ratios.

Excipient screening studies were conducted to increase the compatibility between IGF-I and insulin. A preferred IGF-I formulation was developed for mixing with insulin. It contains 10 mg/ml IGF-I, 160 mM arginine, 10 mM histidine at pH 7.2 and 3 mg/ml phenol. The ability of this arginine formulation to mix with Regular, NPH-, and 70/30 insulin at various mixing ratios was assessed. When this formulation was mixed with Regular insulin, percent soluble IGF-I and insulin were nearly 90% or above for all potential mixing ratios. Mixing of this IGF-I formulation and NPH-insulin at most of the mixing ratios resulted in no change in IGF-I and NPH-insulin before and after mixing. At very low NPH-insulin/IGF-I mixing ratios, portions of NPH-insulin-protamine complex dissociated.

Excipients such as arginine, lysine, glutamate, SDS, and/or certain cyclodextrins were shown to be effective in preventing IGF-I and insulin electrostatic interaction and subsequent precipitation upon mixing. The use of SDS and β-cyclodextrin sulfobutyl ether together with arginine in the IGF-I formulation proved to be extremely effective in allowing IGF-I and Regular insulin to be mixed at a very wide range of mixing ratios. However, they cannot be used to mix with NPH-insulin due to the dissociation of NPH-insulin-protamine complexes in the presence of SDS and β-cyclodextrin sulfobutyl ether.

What is claimed is:

1. A composition comprising a mixture of insulin-like growth factor-I (IGF-I) and hexameric insulin without zinc and protamine (hexameric insulin) and an excipient selected from the group consisting of arginine, lysine, glutamate, sodium dodecyl sulfate, and a combination of beta-hydroxy cyclodextrin and arginine, wherein the IGF-I and hexameric insulin remain completely solvated in the composition, and wherein the hexameric insulin and IGF-I are present in a volume:volume ratio of from about 1:6 to 6:1.

2. The composition of claim 1 wherein the volume:volume ratio of hexatmeric insulin:IGF-I is from about 0.2:1 to 1:1.

3. The composition of claim 1 further comprising phosphate-buffered saline.

4. The composition of claim 1 further comprising a stabilizer.

5. The composition of claim 1 wherein the excipient is arginine and additionaallyl comprising histidine and a phenol.

6. The composition of claim 1 wherein the excipient is sodium dodecyl sulfate in a concentration of about 1–10% and the hexameric insulin and IGF-I are present in a volume:volume ratio of from about 1:1 to 6:1.

7. The composition of claim 1 comprising about 5–20 mg/ml IGF-I, about 2–10 mg/ml hexameric insulin, about 100–200 mM arginine, about 5–20 mM histidiine at pH about 7–7.5, and about 1–5 mg/ml phenol.

8. The composition of claim 1 comprising about 10 mg/ml IGF-I, about 3–4 mg/ml hexameric insulin, about 160 mM arginine, about 10 mM hiscidine at pH 7.2, and about 3 mg/ml phenol.

9. The composition of claim 1 wherein the IGF-I and hexameric insulin are not complexed.

10. The composition of claim 1 wherein the excipient is arginine.

11. The composition of claim 10 wherein two or more of said excipients are used.

12. The composition of claim 1 wherein two or more of said excipients are used.

13. The composition of claim 12 wherein the excipients are arginine, sodium dodecyl sulfate, and beta-cyclodextrin sulfobutyl ether.

14. The composition of claim 1 wherein the excipient is arginine in a concentration of about 100 to 300 mM.

15. The composition of claim 14 further comprising beta-cyclodextrin sulfobutyl ether as excipient in a concentration of about 1–10%.

16. The composition of claim 1 further comprising a buffer.

17. The composition of claim 16 wherein the buffer is at a pH of about 7 to 7.5.

18. The composition of claim 17 wherein the buffer is histidine.

19. A method for preparing the position of claim 1 comprising mixing together as component (a) the IGF-I in an excipient selected from the group consisting of arginine, lysine, glutamic acid, sodium dodecyl sulfate, beta-hydroxy cyclodextrin, and beta-cyclodextrin sulfobutyl ether; and as component (b) the hexaneric insulin.

20. The method of claim 19 further comprising incubating the mixture for a period of time at about 30–40° C., wherein the composition further comprises phosphate-buffered saline.

21. The method of claim 20 wherein the mixture is incubated for about 15 minutes at 37° C.

22. A kit comprising:
(a) a container comprising the composition of claim 1 comprising effective amounts of the hexameric insulin and IGF-I; and
(b) instructions for using the above composition to treat a disorder against which the composition is effective.

23. The kit of claim 22 wherein the disorder is a hyperglycemic disorder.

24. A kit for preparing the composition of claim 1 comprising:
(a) a container comprising the IGF-I in an excipient selected from the group consisting of arginine, lysine, glutamic acid, sodium dodecyl sulfate, and a combination of beta-hydroxy cyclodextrin and arginine;
(b) a container comprising the hexameric insulin; and
(c) instructions for combining the contents of containers (a) and (b).

25. The kit of claim 24 wherein when the IGF-I and hexameric insulin are combined, the composition is a pharmaceutically acceptable formulation.

26. The kit of claim 25 wherein the pharmaceutically acceptable formulation is for treating a hyperglycemic disorder.

27. The kit of claim 24 wherein the excipient is arginine.

28. The kit of claim 27 wherein container (a) comprises about 5–20 mg/ml IGF-I, about 100–200 mM arginine, about 5–20 mM histidine at about pH 7–7.5, and about 1–5 mg/ml phenol.

29. The kit of claim 28 wherein container (a) comprises about 10 mg/ml IGF-I, about 160 mM arginine, about 10 mM histidine at about pH 7.2, and about 3 mg/ml phenol.

30. A composition comprising a mixture of insulin-like growth factor-I (IGF-I) and a mixture of 70% crystal suspension of insulin-protamine complex wherein the crystals contain approximately 0.9 molecules of protamine and two zinc atoms per insulin hexamer and 30% hexameric insulin without zinc and protamine (70%/30% mixture), arginine, histidine, and phenol, wherein the IGF-I and 70%/30% mixture remain completely solvated in the composition, and wherein the 70%/30% mixture and IGF-I are present in a volume:volume ratio of from about 1:1 to 6:1.

31. The composition of claim 30 comprising about 5–20 mg/ml IGF-I, about 100–200 mM arginine, about 5–20 mM histidine at pH about 7–7.5 and about 1–5 mg/ml phenol.

32. The composition of claim 30 comprising about 10 mg/ml IGF-I, about 160 mM arginine, about 10 mM histidine at pH 7.2 and about 3 mg/ml phenol.

* * * * *

UNITED STATES PATENT AND TRADEMARK OFFICE
CERTIFICATE OF CORRECTION

PATENT NO.     : 6,559,122 B1
DATED          : May 6, 2003
INVENTOR(S)    : Oeswein et al It is certified that error appears in the above-identified patent and that said Letters Patent is hereby corrected as shown below:

Column 24,
Lines 44-46, should be changed from "The composition of claim 1 wherein the volume:volume ratio of hexatmeric insulin:IGF-I is from about 0.2:1 to 1:1." to -- The composition of claim 1 wherein the volume:volume ratio of hexameric insulin:IGF-I is from about 0.2:1 to 1:1 --
Lines 51-53, should be changed from "The composition of claim 1 wherein the excipient is arginine and additionaallyl comprising histidine and a phenol." to -- The composition of claim 1 wherein the excipient is arginine and additionally comprising histidine and a phenol.
Line 60, change "100-200 mM arginine, about 5-20 mM histidiine at pH" to -- 100-200 mM arginine, about 5-20 mM histidine at pH --.
Line 64, should be changed from "arginine, about 10mM hiscidine at pH 7.2, and about 3" to -- arginine, about 10mM histidine at pH 7.2, and about 3 --.

Column 25,
Lines 21-26, should be changed from "A method for preparing the position of claim 1 comprising mixing together as component (a) the IGF-I in an excipient selected from the group consisting of arginine, lysine, glutamic acid, sodium dodecyl sulfate, beta-hydroxy cyclodextrin, and beta-cyclodextrin sulfobutyl ether; and as component (b) the hexaneric insulin." to -- A method for preparing the composition of claim 1 comprising mixing together as component (a) the IGF-I in an excipient selected from the group consisting of arginine, lysine, glutamic acid, sodium dodecyl sulfate, beta-hydroxy cyclodextrin, and beta-cyclodextrin sulfobutyl ether; and as component (b) the hexameric insulin. --.

Signed and Sealed this

Sixth Day of July, 2004

JON W. DUDAS
*Acting Director of the United States Patent and Trademark Office*